(12) United States Patent  (10) Patent No.: US 8,034,987 B2
Sekiguchi et al.  (45) Date of Patent: Oct. 11, 2011

(54) PROCESS FOR PRODUCING PROPYLENE AND AROMATIC HYDROCARBONS, AND PRODUCING APPARATUS THEREFOR

(75) Inventors: Mitsuhiro Sekiguchi, Tokyo (JP); Yoshikazu Takamatsu, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 251 days.

(21) Appl. No.: 12/086,308

(22) PCT Filed: Jan. 12, 2007

(86) PCT No.: PCT/JP2007/050311
§ 371 (c)(1), (2), (4) Date: Sep. 29, 2009

(87) PCT Pub. No.: WO2007/080957
PCT Pub. Date: Jul. 19, 2007

(65) Prior Publication Data
US 2010/0022810 A1  Jan. 28, 2010

(30) Foreign Application Priority Data
Jan. 16, 2006 (JP) .................................. 2006-008038

(51) Int. Cl.
*C07C 2/52* (2006.01)
*C07C 4/02* (2006.01)
(52) U.S. Cl. ........ 585/322; 585/330; 585/324; 585/418; 585/653
(58) Field of Classification Search .................. 585/322, 585/330, 324, 418, 653
See application file for complete search history.

(56) References Cited

U.S. PATENT DOCUMENTS

| | | | |
|---|---|---|---|
| 3,518,319 A | 6/1970 | Ellert et al. | |
| 3,756,942 A | 9/1973 | Cattanach | |
| 4,804,801 A | 2/1989 | Yan | |
| 4,990,715 A | 2/1991 | Knox | |
| 5,773,676 A | 6/1998 | Drake et al. | |
| 5,968,342 A | 10/1999 | Tsunoda et al. | |
| 6,307,117 B1 | 10/2001 | Tsunoda et al. | |

FOREIGN PATENT DOCUMENTS

| | | |
|---|---|---|
| EP | 1 770 080 A1 | 4/2007 |
| JP | 49-41322 | 4/1974 |
| JP | 2-184638 | 7/1990 |
| JP | 6-346063 | 12/1994 |
| JP | 8-127546 | 5/1996 |
| JP | 10-52646 | 2/1998 |
| WO | WO-96/13331 | 5/1996 |
| WO | WO-00/10948 | 3/2000 |
| WO | WO-2006-009099 A1 | 1/2006 |

*Primary Examiner* — Thuan Dinh Dang
(74) *Attorney, Agent, or Firm* — Finnegan, Henderson, Farabow, Garrett & Dunner, L.L.P.

(57) ABSTRACT

It is an object of the present invention to provide an improved process whereby the yield structure of the components can be varied by a simple method, and the products can be produced stably and efficiently in a process for producing propylene and aromatic hydrocarbons from a hydrocarbon feedstock containing $C_{4-12}$ olefins using a medium pore diameter zeolite-containing catalyst. A process for producing is disclosed which comprises a propylene production step wherein a specific zeolite catalyst is used to remove a $C_{4+}$ hydrocarbon component from a reaction mixture, and part of the hydrocarbon component is recycled as necessary without modification, and an aromatic hydrocarbon production step wherein all or a part of the $C_{4+}$ hydrocarbon component is used as the raw material.

28 Claims, 3 Drawing Sheets

PROCESS FOR PRODUCING PROPYLENE AND AROMATIC HYDROCARBONS, AND PRODUCING APPARATUS THEREFOR

TECHNICAL FIELD

The present invention relates to a process for producing propylene and aromatic hydrocarbons by catalytic conversion and catalytic cyclization from a hydrocarbon feedstock, and to a producing apparatus therefor.

BACKGROUND ART

Thermal cracking has been widely used for obtaining propylene and aromatic hydrocarbons from hydrocarbon feedstock, but by its very nature thermal decomposition requires severe reaction conditions, and a common by-product is methane, which is difficult to use as petrochemical feedstock. Moreover, the product yields of propylene and other olefins and benzene, toluene and other aromatic hydrocarbons as percentages of the decomposition product are generally limited, and the yield structure is not sufficiently flexible among other problems.

Patent Document 1 discloses a method wherein silver is carried on crystalline aluminosilicate zeolite in order to improve selectivity for lower olefins. Although propylene yield is improved by this method, the yield of aromatic hydrocarbons is poor. Also, in methods for catalytic conversion of hydrocarbons using zeolite, coke accumulates on the catalyst and must be frequently removed by combustion to regenerate the catalyst, but the problem is that in the case of the acid zeolite described above, repeated regeneration operations cause permanent degradation of catalyst activity. This occurs because coke combustion generates steam that hydrolyzes the zeolite, causing aluminum to be released from the zeolite crystals and eliminating protons that are active sites in the catalyst. This poses a serious problem that must be solved if proton-type zeolites are to be used in these kinds of reactions.

Patent Document 2 discloses a proton-free zeolite catalyst along with a method for using this catalyst to convert hydrocarbon feedstock into ethylene, propylene and monocyclic aromatic hydrocarbons. The catalyst used in this method has the advantage of being resistant to regeneration degradation, but is still vulnerable to the problem of coking deterioration. Moreover, because the aforementioned paraffin conversion reaction is an endothermic reaction, a large amount of heat must be supplied to the reaction vessel. As a result, this method requires a complex and expensive reaction system.

An effective means of increasing the flexibility of the propylene/aromatic hydrocarbon yield structure is to obtain these components by separate processes. However, the reaction technologies that have been used for each in the past need to be improved in order to obtain both components efficiently and stably.

For the propylene production step, methods of catalytic conversion from hydrocarbon feedstock containing olefins using catalysts containing zeolite have been adopted, and there are many reports of methods for producing propylene from hydrocarbon feedstock containing olefins by catalytic conversion using catalysts containing zeolite. However, efficient, long-term and stable production of propylene from hydrocarbon feedstock containing olefins by catalytic conversion using a catalyst containing zeolite is difficult for the following reasons.

Propylene is an intermediate in reactions for converting olefins into aromatic hydrocarbons in the presence of a zeolite catalyst, and is converted into aromatic hydrocarbons by the subsequent reaction. Consequently, when attempting to produce propylene by catalytic conversion of hydrocarbon feedstock containing olefins using a catalyst containing zeolite, the catalyst activity and reaction conditions need to be strictly controlled in order to obtain the desired product with a high yield. That is, if the catalyst is too active or the contact time is too long, the resulting propylene will be converted to aromatic hydrocarbons by the subsequent reaction. Conversely, if the catalyst is not active enough or the contact time is too short, the propylene yield will be poor. Because olefins are highly reactive, however, deposition of coke on the surface of the catalyst is likely to occur during catalytic conversion of the hydrocarbon feedstock containing olefins using the catalyst containing zeolite. In continuous conversion reactions, the catalyst deteriorates due to coking (coking deterioration), and catalytic activity quickly declines. Regeneration operations are required as described above in order to reactivate the catalyst, but after repeated regeneration operations catalytic activity can no longer be adequately restored.

As discussed above, coking is particularly likely in catalytic conversion reactions of the hydrocarbon feedstock containing olefins using catalysts containing zeolite, and regeneration degradation is also extremely likely because of the consequent need for frequent regeneration operations.

Patent Document 3 discloses a method for converting $C_{4-12}$ olefins into ethylene and propylene using a proton-free ZSM-5 zeolite containing an IB group metal and having an $SiO_2/Al_2O_3$ ratio of from 200 to 5000. When a zeolite-containing catalyst is used to selectively convert $C_{4-12}$ olefins to propylene, olefins with about 4 to 8 carbon atoms are produced as reaction products in addition to ethylene and propylene. This is because the raw material olefins are dimerized and decomposed by the catalyst, resulting in an olefin composition similar to the equilibrium composition under the reaction conditions. Consequently, in order to efficiently convert the raw material olefins into propylene, the $C_{4+}$ olefins in the reaction product need to be efficiently recycled back to the reaction container by a simple method, and converted to propylene.

Patent Document 3 describes a method for removing the heavy fraction with a boiling point at or above that of the $C_8$ aromatic hydrocarbons from the reaction product and recycling the $C_{4-8}$ olefins back into the reaction vessel, but this method requires multiple separators to obtain the raw material for recycling, thereby complicating the equipment and operations, so there is a demand for simpler methods, but so far it has not been possible to achieve both efficiency (equipment, operating costs and yield) and stable production. Patent Document 3 also makes no mention of the effect on coking deterioration of the diolefin concentration in the hydrocarbon feedstock. The higher the diolefin compound concentration in the hydrocarbon feedstock, the more activity deteriorates due to coke production. Removal of diolefins from the feedstock is highly unpractical on an industrial scale because it requires that the feedstock be purified by pretreatment such as separation by distillation, partial hydrogenation or the like.

For the aromatic hydrocarbon producing step, however, many methods are known for producing aromatic hydrocarbons using zeolite catalysts. As in the propylene producing step, the biggest problems with methods of producing aromatic hydrocarbons by catalytic cyclization using a zeolite catalyst are controlling coking deterioration during the reaction and controlling regeneration (permanent) degradation that occurs when the coke on the deteriorated catalyst is removed by combustion to regenerate the catalyst.

Many proposals have been made in recent years for preventing both kinds of deterioration. Specifically, Patent Document 4 reports that coke precipitation during the reaction and permanent degradation due to dealumination during catalyst regeneration can be simultaneously controlled by using a high-silica zeolite catalyst of a specific particle size that exhibits a specific surface acid site/total acid site ratio and amounts of pyridine adsorption before and after steam treatment, or in other words specific changes in acid site behavior. In this method, however, the preferred method of synthesizing the zeolite is one using a seed slurry, which has low productivity, and moreover the stable production range of ZSM-5 zeolite is narrow, limiting the $SiO_2/Al_2O_3$ ratio so that the primary particles are likely to be relatively large. According to Patent Document 4, both coking deterioration and regeneration degradation are controlled, but because the zeolite particle size is relatively large, it does not appear that coking deterioration is adequately controlled. A zeolite with a smaller primary particle size would be preferable, but according to Patent Document 4 this results in greater accumulation of coke during the reaction, and more rapid regeneration (permanent) degradation. These are serious obstacles to the industrial manufacture of aromatic hydrocarbons.

An example using a proton-free zeolite is given in Patent Document 2. The catalyst used in this method is effective at resisting regeneration degradation as described above, but the problem of coking deterioration remains. Consequently, coking deterioration is likely when the hydrocarbon feedstock contains large amounts of olefins. Moreover, this document makes no mentioned of the effect of the particle size of the zeolite used in the catalytic cyclization reaction.

[Patent Document 1] Japanese Patent Application Laid-open No. H02-184638
[Patent Document 2] WO 1996/013331, pamphlet
[Patent Document 3] WO 2000/010948, pamphlet
[Patent Document 4] Japanese Patent Application Laid-open No. H10-052646

DISCLOSURE OF INVENTION

Problems to be Solved by the Invention

It is an object of the present invention to provide a process for producing propylene and aromatic hydrocarbons from hydrocarbon feedstock containing $C_{4\text{-}12}$ olefins, wherein the yield structure of the two components can be varied by a simple method, along with a producing apparatus.

Means for Solving the Problems

As a result of exhaustive research aimed at solving the aforementioned problems, the inventors in the present invention concluded that it was desirable to produce the different components in separate processes using specific zeolite catalysts in order to easily vary the production ratios of the two target components, propylene and aromatic hydrocarbons, and perfected the present invention based on this finding.

That is, the first aspect of the producing process according to the present invention provides:

[1] a process for producing propylene and aromatic hydrocarbons, comprising:
  (1) a propylene production step wherein a hydrocarbon feedstock containing 50% by mass or more of at least one of $C_{4\text{-}12}$ olefin is brought into contact in a propylene production reactor with a molded catalyst A containing a first zeolite fulfilling conditions (i) through (iv) below to thereby perform a catalytic conversion reaction on the at least one of $C_{4\text{-}12}$ olefin, resulting in a reaction mixture containing propylene, the reaction mixture is separated into fraction C containing mainly hydrogen and $C_{1\text{-}3}$ hydrocarbons and fraction D containing mainly at least one of $C_{4+}$ hydrocarbon, and propylene is isolated from the fraction C:
    (i) having a medium pore diameter zeolite with a pore diameter of from 5 to 6.5 Å;
    (ii) containing substantially no protons;
    (iii) containing at least one metal selected from the group consisting of metals in Group IB of the periodic table; and
    (iv) having an $SiO_2/Al_2O_3$ molar ratio of at least 800 but no more than 2,000; and
  (2) an aromatic hydrocarbon production step wherein a raw material containing entirely or partly all or a part of the fraction D is brought into contact in an aromatic hydrocarbon production reactor with a molded catalyst B containing a second zeolite fulfilling conditions (v) through (vii) below in a gaseous phase at 650° C. or less:
    (v) having a medium pore diameter zeolite with a pore diameter of from 5 to 6.5 Å;
    (vi) with a primary particle diameter in a range of from 0.02 to 0.25 μm; and
    (vii) containing at least one metal element selected from the group consisting of metal elements in group IB of the periodic table,

[2] the process according to item [1], wherein the hydrocarbon feedstock containing 50% by mass or more of at least one of $C_{4\text{-}12}$ olefin which is used in the propylene production step contains 2.5% by mass or less of at least one of $C_{3\text{-}12}$ diolefin compound,

[3] the process according to item [1] or [2], wherein the first zeolite contains silver,

[4] the process according to any one of items [1] to [3], wherein the first zeolite is an MFI zeolite,

[5] the process according to any one of items [1] to [4], wherein a value obtained by dividing an amount of component [% by mass] of the $C_{6\text{-}8}$ aromatic hydrocarbons produced in the propylene production reactor by a hydrocarbon partial pressure [MPa] is 13 or less,

[6] the process according to any one of items [1] to [5], wherein, in the propylene production step, 10% by mass to 95% by mass of the fraction D is recycled back to the propylene production reactor and used as part of the hydrocarbon feedstock,

[7] the process according to any one of items [1] to [6], wherein the fraction C is separated into fraction $C_1$ containing mainly hydrogen and hydrocarbons of 1-2 carbon atoms and fraction $C_2$ containing mainly hydrocarbons of 3 carbon atoms, and at least part of the fraction $C_1$ is recycled back to the propylene production reactor and used as part of the hydrocarbon feedstock,

[8] the process according to any one of items [1] to [7], wherein the propylene production reactor is an adiabatic fixed-bed reactor,

[9] the process according to any one of items [1] to [8], wherein a reaction temperature for the propylene production step is from 500° C. to 580° C., a partial pressure of the hydrocarbon feedstock is from 0.05 to 0.3 MPa, and a weight hourly space velocity of the hydrocarbon feedstock based on a weight of the molded catalyst A is from 2 $hr^{-1}$ to 20 $hr^{-1}$,

[10] the process according to any one of items [1] to [9], wherein the molded catalyst B contains at least one selected from the group consisting of the metals belonging to groups IB, IIB, IIIB and VIII in the periodic table and compounds of these,

[11] the process according to any one of items [1] to [10], wherein the second zeolite contains silver,

[12] the process according to any one of items [1] to [11], wherein the second zeolite is an MFI zeolite,

[13] the process according to any one of items [1] to [12], wherein the aromatic hydrocarbon production reactor is an adiabatic fixed-bed reactor,

[14] the process according to any one of items [1] to [13], wherein the fraction C is separated into fraction $C_1$ containing mainly hydrogen and hydrocarbons of 1-2 carbon atoms and fraction $C_2$ containing mainly hydrocarbons of 3 carbon atoms, and at least part of the fraction $C_1$ is used as part of the hydrocarbon feedstock in the aromatic hydrocarbon production step.

A preferred mode of the first aspect of producing process according to the present invention provides a process for producing propylene and aromatic hydrocarbons from a hydrocarbon feedstock, comprising the steps of:

(1) producing propylene by catalytic conversion from the hydrocarbon feedstock, wherein the hydrocarbon feedstock containing 50% by weight or more of at least one of $C_{4-12}$ olefin is brought into contact in a propylene production reactor with a molded catalyst A containing a first zeolite fulfilling conditions (i) through (iv) below:

(i) the first zeolite is a medium pore diameter zeolite with a pore diameter of from 5 to 6.5 Å

(ii) the first zeolite contains substantially no protons (iii) the first zeolite contains at least one metal selected from the group consisting of the metals in group IB of the periodic table, and (iv) the first zeolite has an $SiO_2/Al_2O_3$ molar ratio of at least 600 but no more than 2,000, thereby performing a catalytic conversion reaction on the at least one of $C_{4-12}$ olefin, resulting in a reaction mixture containing propylene, the reaction mixture is separated into fraction C containing mainly hydrogen and $C_{1-3}$ hydrocarbons and fraction D containing mainly at least one of $C_{4+}$ hydrocarbon, and propylene is isolated from the fraction C, wherein the propylene production process fulfills the following conditions (v) and (vi):

(v) a value obtained by dividing an amount of component [% by mass] of $C_{6-8}$ aromatic hydrocarbons produced in the propylene production reactor by a hydrocarbon partial pressure [MPa] is 13 or less;

(vi) 10 to 95% by mass of the fraction D is recycled back to the propylene production reactor and used as the hydrocarbon feedstock; and (2) producing aromatic hydrocarbons by catalytic cyclization from a hydrocarbon feedstock, wherein a part of the fraction D, as all or part of the hydrocarbon feedstock, is brought into contact in an aromatic hydrocarbon production reactor with a molded catalyst B containing a second zeolite fulfilling conditions (vii) through (ix) below in a gaseous phase at 650° C. or less:

(vii) the second zeolite is a medium pore diameter zeolite with a pore diameter of from 5 to 6.5 Å;

(viii) the second zeolite has a primary particle diameter in the range of from 0.02 to 0.25 μm; and (ix) the second zeolite contains at least one metal selected from the group consisting of the metal elements in group IB of the periodic table, wherein the zeolite-containing molded catalyst B also contains at least one element selected from the group consisting of the elements belonging to groups IB, IIB, IIIB and VIII in the periodic table.

The second aspect of the producing process according to the present invention provides:

[15] a process for producing propylene and aromatic hydrocarbons, comprising:

(1) a propylene production step wherein a hydrocarbon feedstock containing 50% by mass or more of at least one of $C_{4-12}$ olefin is brought into contact in a propylene production reactor with a molded catalyst A containing a first zeolite fulfilling conditions (i) through (iv) below to thereby perform a catalytic conversion reaction on the at least one of $C_{4-12}$ olefin, resulting in a reaction mixture containing propylene, the reaction mixture is separated into fraction E containing mainly hydrogen and $C_{1-2}$ hydrocarbons and fraction F containing mainly at least one of $C_{3+}$ hydrocarbon, the fraction F is separated into fraction $F_1$ containing mainly $C_3$ hydrocarbons and fraction $F_2$ containing mainly at least one of $C_{4+}$ hydrocarbon, and propylene is isolated from the fraction $F_1$:

(i) having a medium pore diameter zeolite with a pore diameter of from 5 Å to 6.5 Å;

(ii) containing effectively no protons;

(iii) containing at least one metal selected from the group consisting of the metals in Group IB of the periodic table; and (iv) having an $SiO_2/Al_2O_3$ mole ratio of at least 800 but no more than 2,000; and (2) an aromatic hydrocarbon production step wherein a raw material containing entirely or partly all or a part of the fraction $F_2$ is brought into contact in an aromatic hydrocarbon production reactor with a molded catalyst B containing a second zeolite fulfilling conditions (v) through (vii) below in a gaseous phase at 650° C. or less:

(v) having a medium pore diameter zeolite with a pore diameter of from 5 Å to 6.5 Å;

(vi) with a primary particle diameter in the range of from 0.02 μm to 0.25 μm; and (vii) containing at least one metal element selected from the group consisting of metal elements in group IB of the periodic table,

[16] the process according to item [15], wherein the hydrocarbon feedstock containing 50% by mass or more of at least one of $C_{4-12}$ olefin which is used in the propylene production process contains 2.5% by mass or less of at least one of $C_{3-12}$ diolefin compound,

[17] the process according to item [15] or [16], wherein the first zeolite contains silver,

[18] the process according to any one of items [15] to [17], wherein the first zeolite is an MFI zeolite,

[19] the process according to any one of items [15] to [18], wherein a value obtained by dividing an amount of component [% by mass] of the $C_{6-8}$ aromatic hydrocarbons produced in the propylene production reactor by a hydrocarbon partial pressure [MPa] is 13 or less,

[20] the process according to any one of items [15] to [19], wherein, in the propylene production process, 10% by mass to 95% by mass of the fraction $F_2$ is recycled back to the propylene production reactor and used as part of the hydrocarbon feedstock,

[21] the process according to any one of items [15] to [20], wherein at least part of the fraction E is recycled back into the propylene production reactor and used as part of the hydrocarbon feedstock,

[22] the process according to any one of items [15] to [21], wherein the propylene production reactor is an adiabatic fixed-bed reactor,

[23] the process according to any one of items [15] to [22], wherein a reaction temperature for the propylene production step is from 500° C. to 580° C., a partial pressure of the hydrocarbon feedstock is from 0.05 MPa to 0.3 MPa, and a weight hourly space velocity of the hydrocarbon feedstock based on a weight of the molded catalyst A is from 2 hr$^{-1}$ to 20 hr$^{-1}$,

[24] the process according to any one of items [15] to [23], wherein molded the catalyst B contains at least one selected from the group consisting of metals belonging to groups IB, IIB, IIIB and VIII in the periodic table and compounds of these,

[25] the process according to any one items [15] to [24], wherein the second zeolite contains silver,

[26] the process according to any one of items [15] to [25], wherein the second zeolite is an MFI zeolite,

[27] the process according to any one of items [15] to [26], wherein the aromatic hydrocarbon production reactor is an adiabatic fixed-bed reactor,

[28] the process according to any one of items [15] to [27], wherein at least part of the fraction E is used as part of the hydrocarbon feedstock in the aromatic hydrocarbon production step.

A preferred mode of the second aspect of the producing process according to the present invention provides a process for producing propylene and an aromatic hydrocarbon from a hydrocarbon feedstock, comprising:

(1) producing propylene by catalytic conversion from the hydrocarbon feedstock, wherein the hydrocarbon feedstock containing 50% by mass or more of at least one of $C_{4-12}$ olefin is brought into contact in a propylene production reactor with a molded catalyst A containing a first zeolite fulfilling conditions (i) through (iv) below:
 (i) the first zeolite is a medium pore diameter zeolite with a pore diameter of from 5 to 6.5 Å;
 (ii) the first zeolite contains substantially no protons;
 (iii) the first zeolite contains at least one metal selected from the group consisting of the metals in group IB of the periodic table; and
 (iv) the first zeolite has an $SiO_2/Al_2O_3$ mole ratio of at least 600 but no more than 2,000, to thereby perform a catalytic conversion reaction on at least one of $C_{4-12}$ olefin, resulting in a reaction mixture containing propylene, the reaction mixture is separated into fraction E containing mainly hydrogen and $C_{1-2}$ hydrocarbons and fraction F containing mainly at least one of $C_{3+}$ hydrocarbon, the fraction F is separated into fraction $F_1$ containing mainly $C_3$ hydrocarbons and fraction $F_2$ containing mainly at least one of $C_{4+}$ hydrocarbons, and propylene is isolated from the fraction $F_1$, wherein the propylene production step fulfills the following conditions (v) and (vi):
 (v) a value obtained by dividing an amount of component [% by mass] of $C_{6-8}$ aromatic hydrocarbons produced in the propylene production reactor by a hydrocarbon partial pressure [MPa] is 13 or less; and
 (vi) 10 to 95% by mass of the fraction $F_2$ is recycled back to the propylene production reactor and used as the hydrocarbon feedstock, and (2) producing aromatic hydrocarbons by catalytic cyclization from the hydrocarbon feedstock, wherein a part of the fraction $F_2$, as all or part of the hydrocarbon feedstock, is brought into contact in an aromatic hydrocarbon production reactor with a molded catalyst B containing a second zeolite fulfilling conditions (vii) through (ix) below in a gaseous phase at 650° C. or less:
 (vii) the second zeolite is a medium pore diameter zeolite with a pore diameter of from 5 to 6.5 Å;
 (viii) the second zeolite has a primary particle diameter in the range of from 0.02 to 0.25 μm;
 (ix) the second zeolite contains at least one metal selected from the group consisting of the metal elements in group IB of the periodic table, wherein this zeolite-containing molded catalyst B also contains at least one selected from the group consisting of the metals belonging to groups IB, IIB, IIIB and VIII in the periodic table.

An aspect of a producing apparatus according to the present invention provides:

[29] a producing apparatus for producing propylene and aromatic hydrocarbons from a hydrocarbon feedstock, comprising:
 (a) a first reactor that receives the hydrocarbon feedstock and produces a reaction mixture containing propylene;
 (b) a separator that receives the reaction mixture and is connected to the first reactor; and
 (c) a second reactor connected to the separator, wherein the aromatic hydrocarbons are produced,

[30] the producing apparatus according to item [29], wherein the separator has a conduit for directly conducting a part of a separated product obtained from the separator to the first reactor and second reactor,

[31] the producing apparatus according to item [29] or [30], wherein a part of a fraction obtained in the separator is recycled and contained in the first reactor,

[32] the producing apparatus according to any one of items [29] to [31], wherein a fraction that is obtained from the separator and contained in the first and second reactors is a fraction containing mainly at least one of $C_{4+}$ hydrocarbon,

[33] the producing apparatus according to any one of items [29] to [32], wherein a part of a fraction containing mainly hydrogen and $C_{1-2}$ hydrocarbons that is obtained from the separator is contained in the first reactor and the second reactor,

[34] the producing apparatus according to any one of items [29] to [33], wherein the separator is a distilling column or flash drum.

Advantageous Effects of the Invention

According to the producing process of the present invention, propylene and aromatic hydrocarbons can be efficiently and stably produced from olefinic hydrocarbon feedstock, and the production ratios thereof can be easily varied as necessary.

Further, the amount of at least one of $C_{3-12}$ diolefin compound contained in the $C_{4+}$ component produced in the propylene production reactor (which is the raw material in the aromatic hydrocarbon production step) is reduced below the amount of diolefin compounds in the hydrocarbon feedstock (which is the raw material in the propylene production step and contains 50% by mass or more of at least one of $C_{4-12}$ olefin). Because they are highly reactive, diolefins are known to promote soiling of the equipment and coking of the catalyst surface, so by reducing the amount of diolefin compounds in the raw material for the aromatic hydrocarbon production step it is possible to achieve more stable continuous operation in the aromatic hydrocarbon production step.

Furthermore, according to the producing apparatus of the present invention, propylene and aromatic hydrocarbons can be efficiently and stably produced from olefinic hydrocarbon feedstocks by using a simple apparatus and especially a single separator.

BEST MODE FOR CARRYING OUT THE INVENTION

Embodiments of the present invention are explained with reference to the drawings. The following embodiments are only examples for explaining the present invention, and the intent is not to limit the present invention only to these embodiments. The present invention can be implemented in a variety of modes as long as these do not depart from the spirits of the present invention.

FIG. 1 shows a schematic view of a producing apparatus according to one embodiment for implementing the producing process according to the present invention. Producing apparatus 1 according to the present invention comprises propylene production reactor 12, which receives the hydrocarbon feedstock and is used to produce a reaction mixture containing propylene by catalytic conversion from the hydrocarbon feedstock, one separator 16 connected to propylene production reactor 12, which receives the aforementioned reaction mixture and is used to separate the reaction mixture into specific fractions and then isolate the propylene, and aromatic hydrocarbon production reactor 18, which receives a part of the specific fractions described above, is connected to separator 16 and is used to produce aromatic hydrocarbons by catalytic cyclization. Each reactor and separator is connected via conduit 20 as shown in FIG. 1. Specifically, separator 16 is connected via a conduit which conducts the separated product obtained in separator 16 directly to propylene production reactor 12 and aromatic hydrocarbon production reactor 18.

Propylene production reactor 12 receives the hydrocarbon feedstock via heat exchanger 10, and a reaction mixture containing propylene is obtained by catalytic conversion inside reactor 12 by means of contact with the zeolite molded catalyst A described below. Note that this heat exchanger 10 can heat the hydrocarbon feedstock being supplied to producing apparatus 1 according to the present invention using the heating value of the hydrocarbon fluid inside propylene production reactor 12. The reaction mixture containing propylene that is obtained in propylene production reactor 12 is compressed as necessary by compressor 14 and sent to separator 16.

A part of the specific fractions separated in separator 16, and specifically a part of the fractions D or $F_2$ described below, are preferably recycled back to propylene production reactor 12, contained in this reactor 12 and subjected to catalytic conversion. This recycling aspect is described below in the context of the propylene production step.

In order for propylene to be efficiently produced in propylene production reactor 12, a value obtained by dividing an amount of component (% by mass) of the $C_{6-8}$ aromatic hydrocarbons produced in the propylene production reactor by the hydrocarbon partial pressure [MPa] is preferably 13 or less, more preferably 10 or less.

In separator 16, propylene is separated from the reaction mixture containing propylene that was obtained in propylene production reactor 12. Modes of separation may include, but are not limited to, a mode by which the reaction mixture is separated into fraction C containing mainly hydrogen and $C_{1-3}$ hydrocarbons and fraction D containing mainly at least one of $C_{4+}$ hydrocarbon, and propylene is isolated from fraction C, and a mode by which the reaction mixture is separated into fraction E containing mainly hydrogen and $C_{1-2}$ hydrocarbons and fraction F containing mainly at least one of $C_{3+}$ hydrocarbon, fraction F is separated into fraction $F_1$ containing mainly $C_3$ hydrocarbons and fraction $F_2$ containing mainly at least one of $C_{4+}$ hydrocarbon, and propylene is isolated from fraction $F_1$. Specific examples of separator 16 may include a distilling column, a flash drum (gas-liquid separator) and the like, and a distilling column is preferred.

Aromatic hydrocarbon production reactor 18 is a reactor for producing aromatic hydrocarbons by catalytic cyclization, and aromatic hydrocarbons are produced as described below by contact with zeolite-containing molded catalyst B (described below) from all or a part of a specific fraction separated by this separator 16, specifically fraction D or fraction $F_2$.

Note that a fixed-bed reactor, moving-bed reactor, fluidized-bed reactor or stream transport system can be used for propylene production reactor 12 and aromatic hydrocarbon production reactor 18, and an adiabatic fixed-bed reactor is preferred. Propylene production reactor 12 and aromatic hydrocarbon production reactor 18 are preferably made primarily of a metal material such as carbon steel or stainless steel.

Producing apparatus 1 according to the present invention is suitable for implementation of the producing process according to the present invention discussed below, which comprises a propylene production step and an aromatic hydrocarbon production step. Separation of the $C_9$+fraction has conventionally been necessary when producing propylene and aromatic hydrocarbons from olefinic hydrocarbon feedstock, but this is not required in producing apparatus 1 for implementing the producing process according to the present invention. Therefore, because producing apparatus 1 according to the present invention comprises propylene production reactor 12 and aromatic hydrocarbon production reactor 18 with only one separator 16 between propylene production reactor 12 and aromatic hydrocarbon production reactor 18, it is a simple apparatus capable of efficiently and stably producing propylene and aromatic hydrocarbons from an olefinic hydrocarbon feedstock.

In the following explanation, the propylene production step and aromatic hydrocarbon production step of the producing process according to the present invention are discussed separately.

[Propylene Production Step]

A hydrocarbon feedstock containing 50% by weight or more of at least one of $C_{4-12}$ olefin is used in the propylene production step.

In the propylene production step, the term "hydrocarbon feedstock" refers to a raw material containing mainly at least one selected from the group consisting of the $C_{1-12}$ hydrocarbons, such as for example the $C_{1-12}$ normal paraffins, isoparaffins, olefins, cycloparaffins (naphthenes) and cycloparaffins having side chain alkyl groups. The term "olefin" used in the producing process according to the present invention refers to cycloparaffins as well as straight-chain, branched and cyclic olefins. If the olefin content is less than 50% by weight, the propylene yield will be insufficient. This hydrocarbon feedstock may also contain, as impurities, small quantities of tert-butanol, methyl tert-butyl ether, methanol and other oxygen-containing compounds.

The hydrocarbon feedstock can be used as is in the propylene production step if the total content of propadiene, butadiene, pentadiene and other diolefin (diene) compounds and methyl acetylene and other acetylene compounds is not more than 2.5% by mass. When more stable propylene production is desired, the content should be 2% by mass or less. These diolefin compounds are highly polymerizable and are known as a cause of coking deterioration. Of course, it is generally desirable to reduce diene compounds as much as possible by a treatment such as distillation, partial hydrogenation or the like, but such pre-treatment is of course extremely impractical for industrial purposes.

Desirable examples of hydrocarbon feedstocks that can be used in the propylene production step include the following. (1) $C_4$ and $C_5$ fractions isolated from products of thermal cracking of naphtha and other petroleum hydrocarbons, and fractions obtained by partial hydrogenation of diolefins into olefins in these $C_4$ and $C_5$ fractions;

(2) Fractions obtained by isolating and removing some or all of the butadiene and isobutene from the aforementioned $C_4$ fractions;

(3) Fractions obtained by isolating and removing some or all of the isoprene and cyclopentadiene from the aforementioned $C_5$ fractions;

(4) $C_4$ fractions and gasoline fractions isolated from products obtained by fluidized catalytic cracking (FCC) of vacuum gas oil and other petroleum hydrocarbons, (5) $C_4$ fractions and gasoline fractions isolated from cokers;

(6) $C_4$ fractions and/or gasoline fractions isolated from hydrocarbons synthesized by Fischer-Tropsch reaction (FT synthesis) from carbon monoxide and hydrogen.

These may be used individually, or two or more may be used as a mixture.

In the propylene production step, the hydrocarbon feedstock such as those described above is brought into contact in propylene production reactor 12 with a specific zeolite-containing molded catalyst to thereby perform a catalytic conversion reaction of at least one of $C_{4-12}$ olefin contained in the hydrocarbon feedstock, producing a reaction mixture containing propylene, and propylene is then separated from the resulting reaction mixture in separator 18.

In the propylene production step, a so-called "medium pore diameter zeolite" with a pore diameter of from 5 to 6.5 Å is used as the zeolite in the aforementioned zeolite-containing molded catalyst A. The term "medium pore diameter zeolite" refers to a zeolite with a range of pore diameters between the pore diameters of small-pore zeolites (typically A-type zeolites) and the pore diameters of large-pore zeolites (typically mordenite and X-type and Y-type zeolites), which zeolite has an 10-membered oxygen ring in the crystal structure. Examples of the medium pore diameter zeolites may include ZSM-5 and so-called pentasil zeolites, which are structurally similar to ZSM-5. These may include ZSM-5, ZSM-8, ZSM-11, ZSM-12, ZSM-18, ZSM-23, ZSM-35 and ZSM-39. Of these zeolites, the most desirable types of zeolites are those represented as MFI structures according to the IUPAC nomenclature for zeolite frameworks, and ZSM-5 is particular desirable. A zeolite similar to ZSM-5 or ZSM-11 as described in P. A. Jacobs and J. A. Martens, "Stud. Surf. Sci. Catal.", 33, p. 167 to 215 (1987, Netherlands) can also be used.

A zeolite containing substantially no protons can be used as the zeolite in zeolite-containing molded catalyst A in the propylene production step. The term "containing substantially no protons" in the producing process according to the present invention means that the amount of proton (i.e., amount of acid) of the zeolite is 0.02 mmol or less per gram of zeolite as measured by the liquid phase ion exchange/filtrate titration method explained below. Preferably, the amount of proton is 0.01 mmol or less per gram of zeolite.

The liquid phase ion exchange/filtrate titration method is described in Intrazeolite Chemistry, "ACS Symp. Ser." 218, p. 369 to 382 (1983, USA); Nihon Kagakukaishi (Bulletin of the Chemical Society of Japan), 3, p. 521 to 527 (1989, Japan) and the like. Using this method, the amount of proton can be measured as follows. A zeolite-containing molded catalyst is calcined in air and then subjected to ion exchange treatment using an aqueous NaCl solution, after which the molded catalyst is collected by filtration, and a filtrate is also obtained. The collected molded catalyst is washed with pure water, and the whole amount of the resultant wash liquid is collected and mixed with the aforementioned filtrate. The amount of proton of the resulting mixed solution is measured by neutralization titration, and a value per weight of the zeolite in the zeolite-containing molded catalyst is given as the amount of proton of the zeolite. Ammonium ion-type zeolites and multivalent metal cation-type zeolites (such as rare earth metal cation-type zeolites) are known to generate protons by heating. Therefore, the zeolite-containing molded catalyst should be calcined prior to measurement of the amount of proton by the aforementioned method.

The zeolite of zeolite-containing molded catalyst A in the propylene production step contains at least one metal selected from the group consisting of metals belonging to Group IB of the period table (hereinafter referred to as "Group IB metals"), or in other words from the group consisting of copper, silver and gold. Of these metals, copper and silver are preferred, and silver is especially preferred. The term "periodic table" in the present specification means the periodic table described on pages 1 to 15 of the CRC handbook of Chemistry and Physics ($75^{th}$ Edition) by David R. Lide et al. (published by CRC Press Inc., 1994-1995).

The term "Containing a Group IB metal" means containing the Group IB metal in the form of the corresponding cations. However, in addition to cations of the Group IB metal the zeolite may further contain the Group IB metal in another form, such as oxide form. Examples of methods of incorporating the Group IB metal into the zeolite may include methods of treating a zeolite containing no Group IB metal by the conventional method, such as ion exchange, impregnation or kneading, and preferably by an ion-exchange method. When the ion-exchange method is used to incorporate the Group IB metal into the zeolite, a salt of the Group IB metal must be used. Examples of the Group IB metal salts may include silver nitrate, silver acetate, silver sulfate, copper chloride, copper sulfate, copper nitrate and gold chloride.

The amount of the Group IB metal contained as Group IB metal cations in the zeolite-containing molded catalyst is not strictly limited, but is preferably from 0.01 to 5% by mass, more preferably from 0.02 to 3% by mass, based on the weight of the zeolite. If the Group IB metal content is less than 0.01% by mass, the catalytic activity of the zeolite-containing catalyst will be unsatisfactory, while addition of more than 5% by mass will generally result in no further improvement in the performance of the zeolite-containing catalyst. The Group IB metal content of the zeolite can be determined by the known method such as x-ray fluorescence analysis.

Because in a preferred embodiment as discussed above the zeolite of zeolite-containing molded catalyst A in the propylene production step contains substantially no protons, the ion-exchange sites remaining after exchange with the Group IB metal cations are preferably ion-exchanged with the cations of at least one of the metal selected from the alkali metals and alkali earth metals. More preferably they are ion-exchanged with the cations of at least one of the metal selected from the alkali metals, and still more preferably with the cations of at least one of the metal selected from the group consisting of sodium and potassium. In other words, the zeolite of the zeolite-containing molded catalyst in the propylene production step is preferably a zeolite that contains both the Group IB metal and at least one of the metal selected from the alkali metals and alkali earth metals.

The method used to incorporate at least one metal selected from the alkali metals and alkali earth metals into the zeolite may be one similar to the method used for incorporating the Group IB metal into the zeolite. The content of the at least one metal selected from the alkali metals and alkali earth metals differs depending on the type of metal, but is preferably in the range of from 0.01 to 0.4% by mass, based on the weight of the zeolite in the case of sodium and 0.01 to 0.8% by mass, based on the weight of the zeolite in the case of potassium.

When preparing zeolite-containing molded catalyst A for use in the propylene production step, there are no particular limits on the number of times or order in which the method for incorporating at least one metal selected from the alkali metals and alkali earth metals into the zeolite and the method for incorporating the Group IB metal are performed. In any case, however, as discussed above, the zeolite must be made to contain the metal in such a way that it also contains substantially no protons. For example, when preparing a silver/sodium cation exchange-type catalyst as the zeolite-containing molded catalyst for the propylene production step, because some of the silver cannot be carried as silver cations if an alkali component is present in the zeolite-containing molded catalyst, the zeolite is preferably converted to a proton type during molding. Thus, the zeolite-containing molded catalyst, which has been molded as a proton-type zeolite, is first exchanged with sodium (preferably using an aqueous sodium nitrate solution) to convert it into a sodium (proton-free) type, and then exchanged with silver cations (preferably using an aqueous silver nitrate solution).

A $SiO_2/Al_2O_3$ molar ratio of the zeolite in zeolite-containing molded catalyst A in the propylene production step is preferably at least 800 but no more than 2,000. If the $SiO_2/Al_2O_3$ molar ratio is less than 800, the zeolite-containing molded catalyst will deteriorate more rapidly due to coking in the conversion reaction, resulting in a greater replacement frequency when the propylene production step is accomplished by a fixed bed 2-reactor swing system for example, and therefore in greater regeneration frequency. Consequently, regeneration degradation is also accelerated. When the hydrocarbon feedstock contains diolefin compounds, moreover, coking deterioration is more severe and the replacement frequency is even greater, which soon makes it difficult to continue stable operation. To avoid this, it is necessary to pre-treat the diolefin compounds in the raw material, which is impractical for industrial purposes.

On the other hand, the $SiO_2/Al_2O_3$ molar ratio of more than 2,000, there is a problem from the standpoint of catalyst preparation. To maintain the catalyst activity of the zeolite-containing molded catalyst A with a high $SiO_2/Al_2O_3$ molar ratio, the ion-exchange rate of the zeolite must be increased so as to adjust the silver content to an equivalent amount. However, the ion-exchange rate declines as the exchange rate increases when preparing the proton-free, IB metal-exchanged catalyst by ion exchange of a zeolite-containing molded catalyst.

To avoid this it is necessary to increase the metal concentration of the exchange liquid. When the $SiO_2/Al_2O_3$ molar ratio of the zeolite exceeds 2,000, it becomes more difficult to accomplish both ion exchange with the alkali metal and ion exchange with the Group IB metal, and a long time and many steps are required for catalyst preparation when the present invention is used industrially. An excess of chemical liquid is also required, thereby greatly increasing the amount of wastewater produced among other problems.

The $SiO_2/Al_2O_3$ molar ratio of the zeolite contained in the zeolite-containing molded catalyst A used in the propylene production step is preferably at least 900 but no more than 1,800, more preferably at least 1,000 but no more than 1,600. WO 2000/010948 discloses a similar zeolite catalyst. However, in this example the focus is on a zeolite with a $SiO_2/Al_2O_3$ molar ratio of 300, and reaction results are only disclosed up to 24 hours. A zeolite catalyst with a $SiO_2/Al_2O_3$ molar ratio of 3,000 has also been described, but this was obtained by compression molding of zeolite powder, and there are no examples of zeolite catalysts that are industrially applicable.

The $SiO_2/Al_2O_3$ molar ratio of the zeolite can be measured by the conventional method, such as for example the method in which the zeolite is completely dissolved in an aqueous alkali solution or aqueous hydrofluoric acid solution, and the resulting solution is analyzed by plasma emission spectrometry or the like to determine the ratio.

A metalloaluminosilicate in which some of the aluminum atoms in the zeolite framework are replaced by atoms of Ga, Fe, B, Cr or the like, or a metallosilicate in which all the aluminum atoms in the zeolite frameworks are replaced by such atoms, can also be used as the zeolite of zeolite-containing molded catalyst A in the propylene production step. In this case, the $SiO_2/Al_2O_3$ molar ratio is calculated after converting the contents of the aforementioned elements in the metalloaluminosilicate or metallosilicate into moles of alumina.

If desired, at least one metal selected from the group consisting of the metals in Groups IIb, III, Vb, VIIb, VIIb and VIII, such as V, Cr, Mo, W, Mn, Pt, Pd, Fe, Ni, Zn, Ga or the like, may be included in zeolite-containing molded catalyst A in the propylene production step in order to suppress coking deterioration and improve the propylene yield.

If desired, the zeolite-containing molded catalyst A in the propylene production step may be heat treated at 500° C. or more in the presence of steam prior to contact with the hydrocarbon feedstock in order to improve the resistance of the zeolite to coking deterioration. This heat treatment is preferably performed at a temperature of at least 500° C. but no more than 900° C. under a steam partial pressure of 0.01 atm or more.

The zeolite-containing molded catalyst A in the propylene production step may suffer from coking deterioration if used in the conversion reaction for a long period of time. The deteriorated catalyst can be regenerated by burning off the coke on the catalyst at a temperature of 400 to 700° C., usually in an atmosphere of air or a gaseous mixture of oxygen and an inert gas (this treatment is hereinafter referred to as "regeneration treatment").

For the zeolite-containing molded catalyst A in the propylene production step, a porous, flame-resistant, inorganic oxide such as alumina, silica, silica/alumina, zirconia, titania, diatomaceous earth or clay is generally mixed as a binder or molding diluent (matrix) with the aforementioned zeolite to obtain a mixture which is then molded, and the resulting molded body is used as the zeolite-containing molded catalyst. When using the matrix or binder, the content thereof is preferably from 10 to 90% by mass, more preferably from 20 to 50% by mass, based on the total weight of the zeolite and the matrix or binder.

In the propylene production step, the reaction container is filled with the zeolite-containing molded catalyst A such as that described above, and a catalytic conversion reaction is performed with at least one $C_{4-12}$ olefin. The catalytic conversion reaction of the $C_{4-12}$ olefin is preferably effected under the reaction conditions described below, whereby the $C_{4-12}$ olefins in the hydrocarbon feedstock are converted to propylene with high selectivity, with substantially no reaction of paraffins coexisting in the hydrocarbon feedstock. The reaction temperature is preferably from 400 to 600° C., more preferably from 500 to 580° C. The pressure of the hydrocarbon feedstock should be low, and is generally from 0.01 to 1 MPa, preferably from 0.05 to 0.3 MPa. The weight hourly space velocity (WHSV) of the hydrocarbon feedstock should be in the range of from 1 to 100 $hr^{-1}$, preferably from 2 to 20 $hr^{-1}$, based on the weight of the zeolite-containing molded catalyst. The contact time between the hydrocarbon feedstock and the zeolite-containing molded catalyst A is preferably 5 seconds or less, more preferably 1 second or less.

The hydrocarbon feedstock may be a mixture with a dilution gas. Examples of the dilution gas may include an inactive gas such as hydrogen, methane, steam, nitrogen or the like, but hydrogen dilution is not desirable. This is because although hydrogen can be used to suppress coking deterioration of the catalyst, it also causes hydrogenation reactions of the resulting propylene and the like, thereby detracting from the propylene purity (propylene/(propylene+propane)). In the producing process according to the present invention, hydrogen dilution is preferably avoided because stable operation with minimal coking deterioration of the catalyst can be achieved without diluting with hydrogen.

When the propylene production step is performed under the aforementioned conditions under which there is substantially no reaction of paraffins, the olefins in the hydrocarbon feedstock selectively undergo a conversion reaction while paraffin conversion reactions are suppressed, and bi-products such as methane, ethane, propane and the like that are produced by paraffin conversion are controlled, facilitating separation and purification of propylene from the reaction mixture.

In the propylene production step, a fixed-bed reactor, moving-bed reactor, fluidized-bed reactor or stream transport system can be used as the propylene production reactor wherein zeolite-containing molded catalyst A is brought into contact with the hydrocarbon feedstock, and a structurally simple adiabatic fixed-bed reactor is preferred.

Because the zeolite-containing molded catalyst A used in the propylene production step resists deterioration due to coking, propylene can be stably produced for a long period of time even using the fixed-bed reactor. The conversion reaction of paraffins is highly endothermic, whereas the conversion reaction of olefins is slightly endothermic or exothermic, depending on the reaction conditions. When olefins in the hydrocarbon feedstock are selectively reacted under the aforementioned conditions under which substantially no reaction of paraffins in the hydrocarbon feedstock occurs, therefore, it is not necessary to supply reaction heat, and a simple reactor system such as the fixed bed, single-stage adiabatic reactor can be used.

Propylene is separated from the propylene-containing reaction mixture thus obtained. Specifically, in the first process of propylene separation the aforementioned reaction mixture is separated into fraction C containing mainly hydrogen and $C_{1-3}$ hydrocarbons and fraction D containing mainly at least one of $C_{4+}$ hydrocarbon, and propylene is separated from fraction C. In the second process, the reaction mixture is separated into fraction E containing mainly hydrogen and $C_{1-2}$ hydrocarbons and fraction F containing mainly at least one of $C_{3+}$ hydrocarbon, fraction F is separated into fraction $F_1$ containing mainly $C_3$ hydrocarbons and fraction $F_2$ containing mainly at least one of $C_{4+}$ hydrocarbon, and propylene is isolated from fraction $F_1$. These separation processes can be accomplished through a combination of various known methods such as fractional distillation, extraction and the like.

As discussed above, in addition to propylene the aforementioned reaction mixture contains $C_{4+}$ olefins and aromatic hydrocarbons. Consequently, a so-called recycling reaction system, in which a part of the $C_{4+}$ olefins in the reaction mixture are recycled back to the reactor and reacted again, can be used to increase the propylene yield based on the weight of the hydrocarbon feedstock containing 50% by mass or more of at least one of $C_{4-12}$ olefin which is the feedstock in this propylene production step, thereby making more effective use of the hydrocarbon feedstock.

In the producing process according to the present invention, a part of fraction D or fraction $F_2$ can be recycled back to the propylene production reactor and used as part of the hydrocarbon feedstock. That is, the simplest possible recycling process can be constructed by using the aforementioned fraction D or $F_2$ as is as a raw material for recycling without any refinement.

In order to efficiently obtain propylene from the recycling process in the propylene production step, a value obtained by dividing the amount of component (% by mass) of the $C_{6-8}$ aromatic hydrocarbons produced in the reactor by the hydrocarbon partial pressure [MPa] is preferably 13 or less, more preferably 10 or less. This calculated value means that it is desirable, in order to efficiently obtain propylene, to minimize production of the $C_{6-8}$ aromatic hydrocarbon component. A decrease in catalytic activity is likely if the value is 13 or more or in other words if the reaction conditions are such that aromatic hydrocarbons are easily produced. When more of the $C_{6-8}$ aromatic hydrocarbon component is produced in the reactor, not only does the propylene yield decrease, but the ratio of $C_{6-8}$ aromatic hydrocarbon components and $C_{6-8}$ aromatic hydrocarbon components in the recycled raw material increases. As a result, accumulation and coking become a problem in the reactor. The advantage of the calculated value of 13 or less is that the ratio of olefin components increases in the $C_{9+}$ component, which converts relatively easily into an aromatic hydrocarbon component, and the propylene yield can be increased by recycling this component.

A propylene production ratio can be easily increased by increasing the recycling ratio. Conversely, the aromatic hydrocarbon production ratio can be increased by either decreasing the recycling ratio in the propylene production step or stopping recycling and supplying more hydrocarbon components to the subsequent aromatic hydrocarbon production step.

The method of suppressing production of $C_{6-8}$ aromatic hydrocarbon components in the propylene production step is not particularly limited, but a normal method is to reduce the olefin conversion ratio of the hydrocarbon feedstock. The olefin conversion ratio here is the olefin conversion ratio based on butene as represented by the following formula.

Olefin conversion ratio (%)={($C_{4+}$ olefin concentration in hydrocarbon feedstock at reactor inlet− butene concentration in hydrocarbon components at reactor outlet)/$C_{4+}$ olefin concentration in hydrocarbon feedstock at reactor inlet}×100

A desirable olefin conversion ratio is 40 to 75% by mass.

The method of reducing the olefin conversion ratio is not particularly limited, but possible methods include raising the weight hourly space velocity of the hydrocarbon feedstock, lowering the reaction temperature, or raising the $SiO_2/Al_2O_3$ molar ratio of the medium pore diameter zeolite in the medium pore diameter zeolite-containing catalyst. Moreover, the zeolite of the present invention, which contains at least one metal element selected from the group consisting of the metal elements in group IB of the periodic table and substantially no protons, produces few $C_{6-8}$ aromatic hydrocarbons in comparison with commonly used H-type zeolites, allowing the olefin conversion ratio to be increased, which has the effect of increasing the propylene yield.

In the propylene production step, the recycling ratio of fraction D or fraction $F_2$ is preferably from 10 to 95% by mass, more preferably from 15 to 90% by mass. If the recycling ratio is less than 10% by mass, the propylene yield will not be greatly improved. If the recycling ratio exceeds 95% by mass, paraffin components contained in the hydrocarbon feedstock and $C_{6-8}$ aromatic hydrocarbon components produced in the reactor will accumulate in large quantities, increasing the burden on the reaction apparatus.

The ratio of $C_{9+}$ hydrocarbon components in fraction D or $F_2$ in the propylene production process is preferably 20% by mass or less, more preferably 15% by mass or less. When the conditions are such that this ratio of $C_{9+}$ hydrocarbon components exceeds 20% by mass, the ratio of aromatic hydrocarbon components in this $C_{9+}$ hydrocarbon component will be greater, and propylene will not be obtained efficiently.

The propylene production step is explained in more detail using an example in which the hydrocarbon feedstock is a $C_4$ fraction (fraction containing mainly $C_4$ hydrocarbons such as butane, isobutane, butene, isobutene and the like) obtained from a steam cracking product of petroleum hydrocarbons.

FIG. 2 shows a preferred embodiment of the recycling reaction system of a propylene production step using a $C_4$ fraction as the hydrocarbon feedstock. A reaction mixture (comprising hydrogen and $C_{1+}$ hydrocarbons) is separated into a fraction containing mainly hydrogen and $C_{1-3}$ hydrocarbons (hereinafter referred to as "$H_2 \sim C_3$ fraction") and a fraction containing mainly at least one $C_{4+}$ hydrocarbon (hereinafter referred to as "$C_4$+fraction"). Examples of the apparatus used for separation ($C_3$ separator) may include a distillation column, flash drum (gas-liquid separator) or the like, preferably a distillation column. Propylene is collected from the resulting $H_2 \sim C_3$ fraction. At least part of the $C_4$+fraction can be recycled back to the reactor and used as part of the propylene production raw material. When the $C_4$+fraction is recycled, the butane contained in the hydrocarbon feedstock is concentrated in the $C_4$+fraction. Since butane therefore accumulates when the entire $C_4$+fraction is recycled, butane accumulation can be controlled if the amount of the $C_4$+fraction that is recycled back to the propylene production reactor is limited to part of the obtained $C_4$+fraction.

The $H_2 \sim C_3$ fraction may be further separated into a fraction containing mainly hydrogen and $C_{1-2}$ hydrocarbons (hereinafter referred to as "$C_2$-fraction") and a fraction containing mainly hydrocarbons with 3 carbon atoms (hereinafter referred to as "$C_3$ fraction"). Examples of the apparatus used for separation ($C_2$ separator) may include a distillation column, flash drum (gas-liquid separator) or the like, preferably a distillation column. Ethylene can be collected from the $C_2$-fraction, or when selectively producing propylene, at least part of this $C_2$-fraction can be recycled back to the reactor, and the ethylene in the $C_2$-fraction can be used as part of the raw material. Because the $C_2$-fraction contains hydrogen, methane and ethane in addition to ethylene, hydrogen, methane and ethane accumulate when the entire $C_2$-fraction is recycled. Therefore, accumulation of hydrogen, methane and ethane can be controlled if the amount of the $C_2$-fraction that is recycled back to the reactor is limited to only part of the obtained $C_2$-fraction.

The aromatic hydrocarbon yield can also be increased by using this $C_2$-fraction as a raw material in the subsequent aromatic hydrocarbon production step. Moreover, propylene collected from the $C_3$ fraction can be used as is as chemical grade propylene if the reaction conditions and separation conditions are set appropriately.

The $C_4$+fraction can also be separated into a fraction containing mainly $C_4$ hydrocarbons (hereinafter referred to as "$C_4$ fraction") and a fraction containing mainly at least one of $C_{5+}$ hydrocarbon (hereinafter referred to as "$C_5$+fraction"). The $C_4$ fraction can be separated from the $C_4$+fraction either before or after the $C_4$+fraction is recycled. Examples of the apparatus used for separation ($C_4$ separator) may include a distillation column, flash drum (gas-liquid separator) or the like, preferably a distillation column. Part of the resulting $C_4$ fraction and/or $C_5$+fraction can be recycled back to the propylene production reactor and used as part of the hydrocarbon feedstock.

FIG. 3 shows another preferred embodiment of a recycling reaction system using a $C_4$ fraction as the hydrocarbon feedstock. A reaction mixture (comprising hydrogen and $C_{1+}$ hydrocarbons) is separated into a fraction containing mainly hydrogen and $C_{1-2}$ hydrocarbons (hereinafter referred to as "$C_2$-fraction") and a fraction containing mainly at least one of $C_{3+}$ hydrocarbon (hereinafter referred to as "$C_3$+fraction"). Examples of the apparatus used for separation ($C_2$ separator) may include a distillation column, flash drum (gas-liquid separator) or the like, preferably a distillation column. Ethylene can also be collected from the $C_2$-fraction. When selectively producing propylene, at least part of this $C_2$-fraction can be recycled back to the propylene reactor as discussed above, and the ethylene in the $C_2$-fraction can be used as part of the raw material. It can also be used as the raw material in the aromatic hydrocarbon production step in order to increase the aromatic hydrocarbon yield.

Likewise, the $C_3$+fraction can be further separated into a fraction containing mainly $C_3$ hydrocarbons (hereinafter referred to as "$C_3$ fraction") and a fraction containing mainly at least one of $C_{4+}$ hydrocarbon (hereinafter referred to as "$C_4$+fraction"). Examples of the apparatus used for separation ($C_3$ separator) may include a distillation column, flash drum (gas-liquid separator) or the like, preferably a distillation column. Moreover, propylene collected from the $C_3$ fraction can be used as is as chemical grade propylene if the reaction conditions and separation conditions are set appropriately.

At least part of the $C_4$+fraction can be recycled back to the reactor and used as part of the propylene production raw material. When the $C_4$+fraction is recycled, the butane contained in the hydrocarbon feedstock is concentrated in the $C_4$+fraction. Since butane therefore accumulates when the entire $C_4$+fraction is recycled, butane accumulation can be controlled if the amount that is recycled back to the reactor is restricted to only part of the obtained $C_4$+fraction. As explained above with reference to FIG. 2, the $C_4$+fraction can also be separated into a fraction containing mainly $C_4$ hydrocarbons (hereinafter referred to as "$C_4$ fraction") and a fraction containing mainly at least one of $C_{5+}$ hydrocarbon (hereinafter referred to as "$C_5$+fraction"). The $C_4$ fraction can be separated from the $C_4$+fraction either before or after the $C_4$+fraction is recycled. Examples of the apparatus used for separation ($C_4$ separator) may include a distillation column, flash drum (gas-liquid separator) or the like, preferably a distillation column. At least part of the resulting $C_4$ fraction and/or $C_5$+fraction can be recycled back to the reactor and used as part of the hydrocarbon feedstock.

[Aromatic Hydrocarbon Production Step]

The zeolite used in zeolite-containing molded catalyst B in the aromatic hydrocarbon production step has a pore diameter of from 5 to 6.5 Å. That is, the "medium pore diameter zeolite" is used. Examples of the medium pore diameter zeolites are given above with reference to the propylene production step. Of these, the most desirable types of zeolites are those represented as MFI structures according to the IUPAC nomenclature for zeolite frameworks, and ZSM-5 is particularly desirable.

The zeolite of the zeolite-containing molded catalyst in the aromatic hydrocarbon production step contains at least one metal selected from the group consisting of metals belonging to Group IB of the period table (hereinafter referred to as "Group IB metals"), or in other words from the group consisting of copper, silver and gold. Of these metals, copper and silver are preferred, and silver is especially preferred.

A "zeolite containing a Group IB metal" in the aromatic hydrocarbon production step is preferably one that contains the Group IB metal in the form of the corresponding cations. The IB metal cations carried by ion exchange on the zeolite used in the aromatic hydrocarbon production step are a cause of cracking activity.

Examples of methods for incorporating the Group IB metal into the zeolite may include methods in which a zeolite containing no Group IB metal is treated by the conventional method, such as ion exchange, impregnation or kneading, and preferably is treated by an ion-exchange method. When the ion-exchange method is used to incorporate the Group IB metal into the zeolite, a salt of the Group IB metal must be used. Examples of Group IB metal salts may include silver nitrate, silver acetate, silver sulfate, copper chloride, copper sulfate, copper nitrate and gold chloride. Silver nitrate or copper nitrate is preferred, and silver nitrate is especially preferred.

An amount of the Group IB metal contained in zeolite-containing molded catalyst B is not strictly limited, but is preferably from 0.01 to 5% by mass, more preferably from 0.02 to 3% by mass, based on the weight of the zeolite. If the Group IB metal content is less than 0.01% by mass, the catalytic activity of the zeolite-containing catalyst will be unsatisfactory, while addition of more than 5% by mass will generally result in no further improvement in the performance of the zeolite-containing catalyst. The amount of the Group IB metal contained in zeolite-containing molded catalyst B can be determined by the known method such as x-ray fluorescence analysis.

As well as being included in the zeolite as cations, the Group IB metal in zeolite-containing molded catalyst B in the aromatic hydrocarbon production step may also be included in a form other than cations as discussed below, such as an oxide form. As discussed below the Group IB metal contributes strong dehydrogenation ability to the catalyst of the present invention, and is included in order to improve the aromatic hydrocarbon yield.

The ion-exchange sites that are not exchanged with Group IB metal cations of zeolite contained in zeolite-containing molded catalyst B in the aromatic hydrocarbon production step are of course exchanged with protons or metal cations, and are preferably exchanged with alkali metal cations or Group IIB, Group IIIB or Group VIII metal cations.

The $SiO_2/Al_2O_3$ molar ratio of the zeolite in zeolite-containing molded catalyst B in the aromatic hydrocarbon production step is preferably at least 60 but no more than 200. If the $SiO_2/Al_2O_3$ molar ratio is less than 60 the catalyst will be somewhat less stable with respect to high-temperature steam and be less resistant to regeneration degradation, which is undesirable because the activity is likely to decline gradually in the course of repeated reaction and regeneration when the present invention is applied industrially. If the $SiO_2/Al_2O_3$ molar ratio exceeds 200, on the other hand, a sufficient amount of Group IB metal will not be carried by ion exchange, detracting from cracking activity and from aromatic hydrocarbon yield. Moreover, in order to maintain the catalytic activity of the zeolite-containing molded catalyst with a high $SiO_2/Al_2O_3$ molar ratio, the ion-exchange ratio of the zeolite needs to be increased so as to adjust the Group IB metal content to an equivalent amount, but the ion-exchange ratio of the Group IB metal then declines, increasing the burden of catalyst preparation, which is highly undesirable for industrial purposes.

The $SiO_2/Al_2O_3$ molar ratio of the zeolite in zeolite-containing molded catalyst B in the aromatic hydrocarbon production step is more preferably at least 80 but no more than 120. The $SiO_2/Al_2O_3$ molar ratio of the zeolite can be determined by the known method, such as for example a method in which the zeolite is completely dissolved in an aqueous alkali solution or aqueous hydrofluoric acid solution, and the resulting solution is analyzed by plasma emission spectrometry or the like to determine the ratio.

A metalloaluminosilicate in which some of the aluminum atoms in the zeolite framework are replaced by atoms of Ga, Fe, B, Cr or the like, or a metallosilicate in which all the aluminum atoms in the zeolite frameworks are replaced by such atoms, can also be used as the zeolite contained in zeolite-containing molded catalyst B in the aromatic hydrocarbon production step. In this case, the $SiO_2/Al_2O_3$ molar ratio is calculated after converting the contents of the aforementioned elements in the metalloaluminosilicate or metallosilicate into moles of alumina.

The primary particle diameter of the zeolite contained in zeolite-containing molded catalyst B in the aromatic hydrocarbon production step is in the range of from 0.02 to 0.25 μm. Preferably, the primary particle diameter is in the range of from 0.02 to 0.2 μm, more preferably from 0.03 to 0.15 μm.

The primary particles of the zeolite contained in zeolite-containing molded catalyst B in the aromatic hydrocarbon production step may be present as individual particles or as secondary aggregates. In most cases the primary particles will aggregate to form secondary particles, and since the primary particles assume various forms, a method of measuring the Feret diameter (see The Society of Chemical Engineers, Japan Ed., Kagaku Kogaku Binran (Chemical Engineering Handbook), Revised $6^{th}$ Edition, p. 233) from a scanning microscope image of zeolite powder taken at 100,000× magnification can be adopted for measuring the primary particle diameter in the present invention. Primary particles having this particle diameter should preferably constitute at least 50% by mass, more preferably at least 80% by mass of the total.

The smaller the particle size of the zeolite, the greater the effective surface area, which is known to be an advantage in terms of both activity and coking deterioration. The particle size of the zeolite is affected not by the particle size of secondary particles formed by aggregation of primary particles, but by the particle size of the primary particles that can be distinguished at 100,000× magnification under a scanning electron microscope. Consequently, in zeolite contained in the zeolite-containing molded catalyst in the present invention the Feret diameter of the primary particles as measured by the scanning electron microscopy of zeolite powder at 100,000× magnification is preferably in the range of from 0.02 to 0.25 μm.

However, the crystal structure of this fine-particle zeolite is unstable, and as described in Japanese Patent Application Laid-open No. H10-052646, the lattice aluminum is easily detached by high-temperature treatment in the presence of steam, and regeneration (permanent) degradation is likely due to this low hot water stability. Surprisingly, however, with the zeolite-containing molded catalyst used in the present invention hot water stability is much improved even in the case of a fine-particle zeolite, and regeneration degradation can be greatly controlled, the amount of coke accumulation can be inhibited. According to the present invention, a zeolite-containing molded catalyst is achieved which is resistant to both the conventional problems of coking deterioration and regeneration degradation.

At least one element selected from the group consisting of the elements belonging to Groups IB, IIB, IIIB and VIII in the period table is included in zeolite-containing molded catalyst B in order to confer strong dehydrogenation ability on the catalyst in the aromatic hydrocarbon production step. The metals copper, zinc, gallium, indium, nickel, palladium and platinum and oxides and complex oxides thereof are preferred, and zinc and zinc compounds are most preferred.

Ion exchange or impregnation is generally used as the method of incorporating metal elements and compounds of metal elements belonging to Groups IB, IIB, IIIB and VIII in the period table into the zeolite-containing molded catalyst B, in order to confer strong dehydrogenation ability on the catalyst in the aromatic hydrocarbon production step. The amount of metal elements and compounds of metal elements belonging to Groups IB, IIB, IIIB and VIII in the period table that is incorporated into the zeolite-containing molded catalyst B is generally from 0.1 to 25 by mass %, preferably from 5 to 20% by mass as elements, in order to confer strong dehydrogenation ability on the zeolite-containing molded catalyst B in the aromatic hydrocarbon production step.

In the zeolite-containing molded catalyst B in the aromatic hydrocarbon production step, a porous, flame-resistant, inorganic oxide such as alumina, silica, silica/alumina, zirconia, titania, diatomaceous earth or clay can generally be used as a binder or molding diluent (matrix). Alumina or silica is preferred, and alumina is especially preferred. A mixture obtained by mixing this with the zeolite described above is molded, and the resulting molded body is used as the zeolite-containing molded catalyst. When using the matrix or binder, the content thereof is preferably from 5 to 50% by mass, more preferably from 10 to 50% by mass, based on the total weight of the zeolite and the matrix or binder.

Zeolite-containing molded catalyst B in the aromatic hydrocarbon production step can be subjected to heat treatment at 500° C. or more in the presence of steam prior to contact with the hydrocarbon feedstock with the aim of improving resistance to coking deterioration. Heat treatment is preferably performed at a temperature of at least 500° C. but no more than 900° C., under a steam pressure of 0.01 atm or more.

When zeolite-containing molded catalyst B in the aromatic hydrocarbon production step contains a mixture of Group IB metal-exchanged zeolite, zinc and a compound thereof and alumina (which is a preferred example of the producing process according to the present invention), high-temperature steam treatment serves to stabilize the zinc component in the catalyst as zinc aluminate, thereby achieving the additional object of greatly controlling scattering loss of zinc in the reaction atmosphere. This effect is extremely advantageous for industrial application of the present invention. The zinc aluminate in the present invention has an x-ray diffraction pattern identical to the pattern given in JCPDS 5-0669NBS Circ., 539, Vol. II, 38 (1953).

In a preferred example of the producing process according to the present invention, in the aromatic hydrocarbon production step an aromatic hydrocarbon production reactor is filled with a specific zeolite-containing molded catalyst B such as that described above, which is then brought into contact with the hydrocarbon feedstock (described below) to perform the catalytic cyclization reaction and obtain aromatic hydrocarbons. The aromatic hydrocarbons are separated and collected from the resulting reaction mixture by known methods.

For the hydrocarbon feedstock in the aromatic hydrocarbon production step, a fraction containing at least one of $C_{4+}$ hydrocarbon produced in the propylene production step described above is used as all or a part of the hydrocarbon feedstock. Similarly, a $C_2$-fraction produced in the propylene production step can be used as a raw material, or light hydrocarbon components may be newly added as a raw material.

The light hydrocarbon feedstock that is newly added in the aromatic hydrocarbon production step is a light hydrocarbon feedstock containing at least one selected from the olefins and paraffins, wherein the hydrocarbons have 2 or more carbon atoms and a 90% distillation temperature of 190° C. or less. Examples of such paraffins may include ethane, propane, butane, pentane, hexane, heptane, octane and nonane. Examples of such olefins may include ethylene, propylene, butene, pentene, hexene, heptene, octene and nonene. In addition, cyclopentene, methylcyclopentane, cyclohexene and other cycloparaffins, cyclopentene, methylcyclopentene, cyclohexane and other cycloolefins and/or cyclohexadiene, butadiene, pentadiene, cyclopentadiene and other dienes may be included. A mixture of such hydrocarbons may be used as the raw material, or methane, hydrogen or an inert gas such as nitrogen, carbon dioxide, carbon monoxide or the like may be included in the mixture as a diluent.

These diluents may constitute preferably 20% or less, more preferably 10% or less by volume. It is particularly desirable to use a mixture containing saturated hydrocarbons and unsaturated hydrocarbons at a weight ratio of between 1/0.33 and 1/2.33. The weight ratio of saturated hydrocarbons to unsaturated hydrocarbons here means the weight ratio in the supplied mixture.

Desirable examples of light hydrocarbon components to be newly added to a fraction containing mainly at least one of $C_{4+}$ hydrocarbon produced in the propylene production step may include the following as above:

(1) $C_4$ and $C_5$ fractions isolated from thermal decomposition products of naphtha and other petroleum hydrocarbons, and fractions obtained by partial hydrogenation of diolefins into olefins in these $C_4$ and $C_5$ fractions;

(2) Fractions obtained by isolating and removing some or all of the butadiene and isobutene from the aforementioned $C_4$ fraction;

(3) Fractions obtained by isolating and removing some or all of the isoprene and cyclopentadiene from the aforementioned $C_5$ fraction;

(4) $C_4$ fractions and/or gasoline fractions isolated from products obtained by fluidized catalytic cracking (FCC) of vacuum gas oil and other petroleum hydrocarbons, (5) $C_4$ fractions and/or gasoline fractions isolated from cokers; and (6) $C_4$ fractions and/or gasoline fractions isolated from hydrocarbons synthesized by Fischer-Tropsch reaction (FT synthesis) from carbon monoxide and hydrogen.

In the aromatic hydrocarbon production step, the light hydrocarbon feedstock may also contain, as impurities, tert-butyl alcohol, methyl tert-butyl ether, methanol and other oxygen-containing compounds.

The reaction conditions for the aromatic hydrocarbon production step differ according to the light hydrocarbon feedstock and particularly according to the weight ratios of olefins and paraffins in the feedstock, but a temperature of from 300 to 650° C., a hydrocarbon partial pressure of between atmospheric pressure and 30 atmospheres, and a weight hourly space velocity (WHSV) of from 0.1 to 50 $hr^{-1}$ based on the weight of the zeolite-containing molded catalyst are preferred. More preferably the reaction temperature is in the range of from 400 to 600° C.

A fixed-bed reactor, moving-bed reactor, fluidized-bed reactor or stream transport system can be used for the aromatic hydrocarbon production reactor in the aromatic hydrocarbon production step, and a structurally simple adiabatic fixed-bed reactor is preferred.

Zeolite-containing molded catalyst B in the aromatic hydrocarbon production step may suffer from coking deterioration if used in the conversion reaction for a long period of time. The deteriorated catalyst can be regenerated by burning off the coke on the catalyst at a temperature of from 400 to 700° C., usually in an atmosphere of air or a gaseous mixture of oxygen and an inert gas (this treatment is hereinafter referred to as "regeneration treatment").

Because the zeolite-containing molded catalyst B in the aromatic hydrocarbon production step is resistant to deterioration from coking, aromatic hydrocarbons can be stably produced over a long period of time even using a fixed-bed reactor. Since the zeolite-containing molded catalyst in the producing process according to the present invention is less liable to dealumination in the presence of high-temperature steam, it also resists permanent degradation (regeneration degradation) during regeneration treatment, and consequently suffers very little loss of activity even after repeated reaction and regeneration. Therefore, an aromatic hydrocarbon compound can be produced stably and with high yield over a long period of time. These features are extremely useful for industrial application of the present invention.

EXAMPLES

The present invention is explained in more detail below by means of examples and comparative examples, but the present invention is in no way limited by these examples. Measurements in the examples and comparative examples are performed as follows.

(1) Measurement of the Amount of Proton by Liquid Phase Ion Exchange/Filtrate Titration 2.5 g of zeolite-containing molded catalyst that had been ground in a mortar and baked in air at from 400 to 600° C. was subjected to ion-exchange treatment for 10 minutes with ice cooling in 25 ml of 3.4 mol/liter NaCl aqueous solution. The resulting mixture was filtered, the molded catalyst was washed with 50 ml of pure water, and whole amount of the filtrate including the wash water was recovered. This filtrate (including wash water) was analyzed by neutralizing titration with 0.1 N NaOH aqueous solution, the amount of proton was determined from the neutralization point, and the amount of proton based on zeolite weight was determined based on the zeolite content of the zeolite-containing molded catalyst.

(2) Measurement of Zeolite $SiO_2/Al_2O_3$ Molar Ratio 0.2 g of zeolite was added to 50 g of 5 N NaOH aqueous solution. This was transferred to a stainless steel microcylinder with a Teflon® inner tube, and the microcylinder was sealed. This was then maintained for 15 to 70 hours in an oil bath to completely dissolve the zeolite. The resulting zeolite solution was diluted with ion-exchanged water, the silicon and aluminum concentrations in the diluted liquid were measured with a plasma spectrometer (ICP unit), and the $SiO_2/Al_2O_3$ molar ratio of the zeolite was calculated from the results.

ICP unit and measurement conditions
Device: JOBIN YVON (JY138 ULTRACE), Rigaku Corp.
Measurement Conditions:

| | |
|---|---|
| Silicon measurement wavelength | 251.60 nm |
| Aluminum measurement wavelength | 396.152 nm |
| Plasma power | 1.0 kw |
| Nebulizer gas | 0.28 L/min |
| Sheath gas | 0.3 to 0.8 L/min |
| Coolant gas | 13 L/min |

(3) Measurement of Zeolite Primary Particle Diameter

A zeolite powder sample was held with carbon adhesive tape on an aluminum sample platform, and subjected to Pt deposition with an ion sputterer (Hitachi E-1030) to maintain conductivity.

SEM images were taken with a Hitachi FE-SEM (S-800), at an acceleration voltage (HV) of 20 KV at magnifications of 500, 15,000 and 100,000.

Secondary particles are often formed by aggregation of fine primary particles in the zeolite used in the present invention, so the Feret diameters of 20 or more primary particles that were determined to be primary particles because they appeared as single masses without cracks in the 100,000× scanning electron microscope image were measured, and the average was given as the primary particle diameter. When the primary particle diameter was so large that it could not be evaluated in a 100,000× scanning electron microscope image, a scanning electron microscope image of a different magnification was selected appropriately for purposes of comparison, and the primary particle diameter was determined in the same way.

(4) Gas Chromatography Analysis of Reaction Products
Device: Shimadzu GC-17A
Column: Supelco (U.S.) SPB-1 custom capillary column (inner diameter 0.25 mm, length 60 m, film thickness 3.0 µm)
Sample gas volume: 1 ml (sampling line maintained at 200 to 300° C., liquefaction prevented)
Temperature program: Maintained for 12 minutes at 40° C., then raised to 200° C. at 5° C./minute, then maintained for 22 minutes at 200° C.
Split ratio: 200:1
Carrier gas (nitrogen) flow rate: 120 ml/minute
FID detector: Air supply pressure 50 kPa (about 500 ml/minute), hydrogen supply pressure 60 kPa (about 50 ml/minute)
Measurement method: A thermal conductivity detector (TCD) and hydrogen flame ionization detector (FID) were connected in a line, hydrogen and $C_1$ and $C_2$ hydrocarbons were detected with the TCD detector, and $C_{3+}$ hydrocarbons were detected with the FID detector. 10 Minutes after the start of analysis, detector output was switched from TCD to FID.

(5) Reaction Conversion Ratio, Reaction Rate Constant

The reaction rate constant K, which is an indicator of catalytic activity, was determined by the following formula.

Reaction rate constant $K = WHSV \times \ln[1/(1-X)]$

[wherein X is the olefin conversion ration based on butene {($C_{4-8}$ olefin concentration in raw materials−butene concentration in product)/$C_{4-8}$ olefin concentration in raw materials}].

Example 1

An Na-type ZSM-5 extrudate with a $SiO_2/Al_2O_3$ molar ratio of 1200 (containing 30% by mass of $SiO_2$ binder, 1.6 mmϕ, purchased from Nikki Universal Co., Ltd., Japan) was dispersed in an 0.02 N aqueous silver nitrate solution (10 cc/g-molded zeolite), and subjected to ion-exchange treatment at 60° C. for 1 hour, a treatment that was repeated twice. This was then filtered, water-washed and dried to prepare catalyst A-1. The Ag content of catalyst A-1 as measured by fluorescent x-ray analysis was 0.22% by mass.

A Hastelloy C reactor with an inner diameter of 27 mm was filled with catalyst A-1, which was then steamed for 5 hours under conditions of temperature 650° C., steam flow rate 214 g/hr, nitrogen flow rate 400 NL/hr, and pressure 0.1 MPaG. After steaming treatment, the amount of proton of catalyst A-1 was 0.002 mmol/g as determined by liquid phase ion exchange/filtrate titration. 60 g of the steamed catalyst A-1 was packed in a Hastelloy C reactor with an inner diameter of 27 mm.

The $C_4$ raffinate-2 (hydrocarbons obtained by extracting and removing the butadiene and isobutene from a $C_4$ fraction obtained by steam cracking of naphtha) shown in Table 1 was used as the raw material and supplied at a $C_4$ raffinate-2 supply rate of 360.0 g/hr (WHSV=6 hr$^{-1}$) and a steam supply rate of 108 g/hr to the reactor filled with catalyst A-1 in thereby perform a propylene production reaction under conditions of reaction temperature 550° C., reaction pressure 0.1 MPaG, and the resulting reaction product was supplied to a distillation column and separated into a $H_2$~$C_3$ fraction and a $C_4$+fraction. This propylene production reaction was continued for 2 days.

The product yields (% by mass) are shown in Table 1. The value obtained by dividing the amount of component (% by mass) of the $C_{6-8}$ aromatic hydrocarbons produced in the reactor by the hydrocarbon partial pressure [MPa] was 9.9.

The primary particle size of the zeolite was 0.06 μm as measured by scanning electron microscopy with a magnification of 100,000×. 72 parts by mass of H-type ZSM-5 ($SiO_2$/$Al_2O_3$ molar ratio=92), zinc nitrate hexahydrate (10 parts by mass as zinc metal) and alumina sol (18 parts by mass as $Al_2O_3$) were kneaded and extrusion molded to 1.6 mm in diameter, 4 to 6 mm in length. After being dried at 120° C. for 4 hours, this was baked for 3 hours at 500° C. to obtain a molded catalyst containing zinc carried on zeolite. This catalyst was dispersed in a 1 N sodium nitrate aqueous solution (10 cc/g-molded zeolite), and subjected to ion-exchange treatment three times at room temperature for 1 hour each time. This was then filtered, water washed and dried. This was dispersed in a 0.1 N silver nitrate aqueous solution (10 cc/g-molded zeolite), and subjected to ion exchange for 2 hours at room temperature. This was then filtered, water washed and dried to prepare catalyst B-1.

The Ag content of catalyst B-1 as measured by fluorescence x-ray analysis was 1.8% by mass.

A Hastelloy C reactor with an inner diameter of 27 mm was filled with catalyst B-1, which was then steamed for 3 hours under conditions of temperature 650° C., steam flow rate 214 g/hr, nitrogen flow rate 400 NL/hr, and pressure 0.1 MPaG. After steaming treatment, 35 g of catalyst B-1 was packed in a Hastelloy C reactor with an inner diameter of 27 mm.

Using this reactor, an aromatic hydrocarbon production reaction was continued for 2 days with the $C_4$+fraction obtained from the previous propylene production reaction supplied at a rate of 98 g/hr with a reaction temperature of 515° C. at a pressure of 0.5 MPa. The yield of $C_{6-9}$ aromatic hydrocarbons was 47.4% by mass 8 hours after the start of the reaction and 46.7% by mass after 48 hours.

As calculated based on the $C_4$ raffinate-2, the yield was 26.8% by mass for propylene and 30.6% by mass for $C_{6-9}$ aromatic hydrocarbons.

As shown in Table 1, the raw material in the aromatic hydrocarbon production reaction (the $C_4$+fraction obtained in the previous propylene production reaction) contains fewer diene compounds than $C_4$ raffinate-2. Diene compounds are highly polymerizable and not only promote soiling of the equipment but are also known to be a cause of coking deterioration, so more stable operation can be achieved in the aromatic hydrocarbon production step if the propylene production step is performed first.

Example 2

60 g of catalyst A-1 that had been steamed as in Example 1 was packed in a Hastelloy C reactor with an inner diameter of 27 mm.

Using $C_4$ raffinate-2 shown in Table 1 as the raw material, a propylene production reaction was performed with a reaction temperature of 550° C., a $C_4$ raffinate-2 supply rate of 220.3 g/hr, a recycled $C_4$+fraction supply rate of 139.7 g/hr (WHSV=6 hr$^{-1}$), a steam supply rate of 108 g/hr and a reaction pressure of 0.1 MPaG, the resulting reaction product was supplied to a distillation column and separated into a $H_2$~$C_3$ fraction and a $C_4$+fraction, and about 56% of the $C_4$+fraction was recycled back to the reactor.

The propylene production reaction was continued for 2 days, after which the catalyst was regenerated under the following conditions: regeneration temperature 500 to 550° C., regeneration pressure 0.5 MPaG, nitrogen+air flow rate 1008 NL/hr, oxygen concentration 1 to 5 vol %, regeneration time 10 hours. The yields based on $C_4$ raffinate-2 (% by mass) are shown in Table 1. The value obtained by dividing the amount of component (% by mass) of the $C_{6-8}$ aromatic hydrocarbons produced in the reactor by the hydrocarbon partial pressure [MPa] was 8.9. During regeneration treatment the regeneration gas was sampled periodically at the reactor outlet, the $CO_2$ and CO concentrations were measured, and the amount of coke was determined from these values. The coke yield was 72 ppm by mass as determined by dividing the amount of coke by the total amount of raw materials fed into the reaction.

An aromatic hydrocarbon production reaction was continued for 2 days under the same conditions as in Example 1 except that the raw material was the $C_4$+fraction obtained in this Example 2. The yield of $C_{6-9}$ aromatic hydrocarbons was 44.7% by mass 8 hours after the start of the reaction, and 43.9% by mass after 48 hours.

As converted to yields based on $C_4$ raffinate-2, the propylene yield was 38.1% by mass and the $C_{6-9}$ aromatic hydrocarbons yield was 22.3% by mass.

Example 3

A propylene production reaction was performed under the same conditions as in Example 2 except that the $C_4$ raffinate-2 supply rate was 279.1 g/hr, the recycled $C_{4+}$+fraction supply rate was 80.9 g/hr (WHSV=6 hr$^{-1}$), and about 33% of the $C_{4+}$+fraction was recycled back to the reactor. The yields based on the $C_4$ raffinate-2 (% by mass) are shown in Table 1. The propylene yield based on $C_4$ raffinate-2 was 33.24% by mass 2 hours after the start of the reaction, and 31.35% by mass 48 hours after the start of the reaction. The value obtained by dividing the amount of component (% by mass) of the $C_{6-8}$ aromatic hydrocarbons produced in the reactor by the hydrocarbon partial pressure [MPa] was 4.8.

An aromatic hydrocarbon production reaction was performed under the same conditions as in Example 1 except that the raw material was the $C_4$+fraction obtained in this Example 3. The yield of $C_{6-9}$ aromatic hydrocarbons was 46.3% by mass 8 hours after the start of the reaction and 45.5% by mass after 48 hours.

The yields based on $C_4$ raffinate-2 were 32.4% by mass for propylene and 26.5% by mass for $C_{6-9}$ aromatic hydrocarbons.

The results of Examples 1 to 3 show that the production rates of the desired propylene and $C_{6-9}$ aromatic hydrocarbons can be varied by means of simple changes in the operating conditions even using the same raw material.

Comparative Example 1

A molded catalyst containing H-type ZSM-5 with a $SiO_2/Al_2O_3$ molar ratio of 407 (containing 30% by mass of $SiO_2$ binder, 1.6 mmϕ*5 to 10 mmL) was dispersed in a 1 N aqueous sodium nitrate solution (10 cc/g-molded zeolite), and was subjected to ion-exchange treatment for 1 hour at room temperature, a treatment that was repeated three times. This was then filtered, water-washed and dried to prepare a Na-type ZSM-5/$SiO_2$ molded catalyst. This was dispersed in 0.00145 N aqueous silver nitrate solution (10 cc/g-molded zeolite), and subjected to ion-exchange treatment for 2 hours at room temperature. This was then filtered, water-washed and dried to prepare catalyst A-2.

The Ag content of the catalyst A-2 as measured by fluorescence x-ray analysis was 0.094% by mass.

A Hastelloy C reactor with an inner diameter of 27 mm was filled with catalyst A-2, which was then steamed for 5 hours under conditions of temperature 650° C., steam flow rate 218 g/hr, and nitrogen flow rate 220 NL/hr.

After steaming treatment, the amount of proton of catalyst A-2 was 0.0016 mmol/g-zeolite as determined by liquid phase ion exchange/filtrate titration.

A reaction evaluation test was performed as in Example 3 except that the steamed catalyst A-2 was used. The propylene yield based on $C_4$ raffinate-2 was 27.33% by mass 2 hours after the start of the reaction and 22.61% by mass 48 hours after the start of the reaction, giving a somewhat high propylene yield differential of 4.7% by mass.

An aromatic hydrocarbon production reaction was performed under the same conditions as in Example 1 except that the $C_4$+fraction obtained in this Comparative Example 1 was used as the raw material. The yield of $C_{6-9}$ aromatic hydrocarbons was 47.9% by mass 2 hours after the start of the reaction and 48.0% by mass after 48 hours.

As calculated from these results, the yields based on $C_4$ raffinate-2 were 24.8% by mass for propylene and 30.8% by mass for $C_{6-9}$ aromatic hydrocarbons.

Comparing Example 3 with Comparative Example 1, not only did the combined yield of propylene and $C_{6-9}$ aromatic hydrocarbons drop from 58.9% by mass (Example 3) to 55.5% by mass (Comparative Example 1), but there was greater fluctuation in propylene yield.

The following are reference example involving only propylene production reactions.

Reference Example 1

A H-type ZSM-5 extrudate with a $SiO_2/Al_2O_3$ molar ratio of 1000 (containing 30% by mass of $SiO_2$ binder, 1.6 mmϕ, purchased from Nikki Universal Co., Ltd., Japan) was dispersed in a 1 N sodium nitrate aqueous solution (10 cc/g-molded zeolite), and subjected to ion-exchange treatment at room temperature for 1 hour, a treatment that was repeated 3 times. This was then filtered, water-washed and dried to prepare Na-type ZSM-5/$SiO_2$. This was dispersed in a 0.01 N silver nitrate aqueous solution (10 cc/g-molded zeolite), and subjected to ion-exchange treatment for 2 hours at room temperature. This was then filtered, water-washed and dried to prepare catalyst A-3. The Ag content of catalyst A-3 as measured by fluorescence x-ray analysis was 0.15% by mass.

A quartz glass reactor with an inner diameter of 16 mm was filled with catalyst A-2, which was then steamed for 5 hours under conditions of temperature 650° C., steam flow rate 27.6 g/hr, and nitrogen flow rate 140 Ncc/min. After steaming treatment, the amount of proton of catalyst A-3 was 0.002 mmol/g-zeolite as determined by liquid phase ion exchange/filtrate titration.

A Hastelloy C reactor with an inner diameter of 17 mm was filled with 10 g of the steamed catalyst A-3.

Using this reactor and the $C_4$ raffinate-2 shown in Table 2 as the raw material, a propylene production reaction was performed with a $C_4$ raffinate-2 supply rate of 60 g/hr (weight hourly space velocity (WHSV)=6 $hr^{-1}$), a reaction temperature of 580° C. and a pressure of 0.1 MPaG, the resulting reaction product was cooled to about 30° C. with a heat exchanger at the reactor outlet and conveyed to a gas-liquid separation drum, and the liquid ($C_4$+fraction) was separated and collected. The composition of the collected $C_4$+fraction is shown in Table 2.

Next, a $C_4$+ recycling test was performed for 24 hours under the following test conditions using the collected $C_4$+fraction and $C_4$ raffinate-2 as the raw materials:

Reaction temperature 580° C., $C_4$ raffinate-2 supply rate 30 g/hr, $C_4$+fraction supply rate 31.2 g/hr (WHSV=6.1 $hr^{-1}$), reaction pressure 0.1 MPaG.

The analysis result for the reaction product 12 hours after the start of the reaction was a propylene yield of 32.1% by mass based on the $C_{4-8}$ olefins in the supplied raw material. However, the $C_{6-8}$ component in the collected $C_4$+fraction was considered to be all olefins apart from the aromatic hydrocarbons. The ratio of the reaction rate constants K 4 hours and 24 hours after the start of the reaction [K(24 hrs)/K(4 hrs)] was 0.90.

Reference Example 2

A propylene production reaction was performed with $C_4$ raffinate-2 under the same conditions as in Reference Example 1 except that only 60 g/hr (WHSV=6 $hr^{-1}$) of $C_4$ raffinate-2 was supplied as the raw material to the reactor. The analysis result for the reaction product 12 hours after the start of the reaction was a propylene yield of 31.1% by mass based on the $C_{4-8}$ olefins in the supplied raw material. The ratio of the reaction rate constants K 4 hours and 24 hours after the start of the reaction [K(24 hrs)/K(4 hrs)] was 0.87.

From comparing Reference Examples 1 and 2, it can be seen that there is no ill effect on deterioration of the catalyst even if the $C_4$+fraction is used as is as a recycled material without removing the heavy component. The rise in propylene yield from 31.1% by mass (Reference Example 2) to 32.1% by mass (Reference Example 1) is due to propylene production from the $C_{9+}$ component.

Example 4

A H-type ZSM-5 extrudate with a $SiO_2/Al_2O_3$ molar ratio of 1220 (containing 30% by mass of $SiO_2$ binder, 1.6 mmϕ) was dispersed in a 1 N sodium nitrate aqueous solution (10 cc/g-molded zeolite), and subjected to ion-exchange treatment at room temperature for 1 hour, a treatment that was repeated 3 times. This was then filtered, water-washed and dried to prepare Na-type ZSM-5/$SiO_2$. This was dispersed in a 0.0017 N silver nitrate aqueous solution (10 cc/g-molded zeolite), and subjected to ion-exchange treatment for 2 hours at room temperature. This was then filtered, water-washed and dried to prepare catalyst A-4. The Ag content of catalyst A-4 as measured by fluorescence x-ray analysis was 0.095% by mass.

A Hastelloy C reactor with an inner diameter of 27 mm was filled with catalyst A-4, which was then steamed for 5 hours under conditions of temperature 650° C., steam flow rate 214 g/hr, nitrogen flow rate 400 NL/hr, and pressure 0.1 MPaG. After steaming treatment, the amount of proton of catalyst A-4 was 0.002 mmol/g as determined by liquid phase ion exchange/filtrate titration. 60 g of the steamed catalyst A-4 was packed in a Hastelloy C reactor with an inner diameter of 27 mm.

Using this reactor and the $C_4$ raffinate-2 shown in Table 3 as the raw material, a propylene production reaction was performed with a $C_4$ raffinate-2 supply rate of 268.7 g/hr, a recycled $C_4$+fraction supply rate of 181.3 g/hr (WHSV=7.5 hr$^{-1}$), a reaction temperature of 550° C. and a reaction pressure of 0.1 MPaG, the resulting reaction product was supplied to a distillation column, the $H_2$–$C_3$ fraction and $C_4$+fraction were separated, and about 58% of the $C_4$+fraction was recycled back to the reactor. The propylene yield [% by mass] based on the $C_4$ raffinate-2 was 32.9% by mass 2 hours after the start of the reaction and 30.4% by mass after 48 hours.

An aromatic hydrocarbon production reaction was performed under the same conditions as in Example 1 except that the $C_4$+fraction obtained in this Example 4 was used as the raw material. The yield of $C_{6-9}$ aromatic hydrocarbons was 45.5% by mass 2 hours after the start of the reaction and 45.2% by mass after 48 hours.

As calculated from these results, the yields based on $C_4$ raffinate-2 were 31.7% by mass for propylene and 24.8% by mass for aromatic hydrocarbons.

This shows that two days of continuous operation can be accomplished without any ill effect on deterioration even using a raw material wherein the diolefin compound concentration is 2.25% by mass.

Example 5

A reaction was performed under the same conditions as the aromatic hydrocarbon production reaction of Example 2 except that a mixture of the $C_4$+fraction (60 g/hr) obtained in Example 3 and the $C_5$ fraction shown in Table 3 (38 g/hr) was supplied as the raw material. The $C_{6-9}$ aromatic hydrocarbon yield was 44.1% by mass 8 hours after the start of the reaction and 43.2% by mass after 48 hours.

The ratio of the aromatic hydrocarbon component can be increased by adding a fresh light hydrocarbon component as in Example 5. Specifically, when 60 g/hr of the $C_4$+fraction obtained in Example 3 was used as the raw material the $C_{6-9}$ aromatic hydrocarbon yield 8 hours after the start of the reaction was 46.3% by mass, or 60 g/hr×0.463=27.8 g/hr. By contrast, when the mixture of Example 5 was used as the raw material, the $C_{6-9}$ aromatic hydrocarbon yield 8 hours after the start of the reaction was 44.1% by mass, or (60+38)g/hr× 0.441=41.0 g/hr. This shows that the proportion of the aromatic hydrocarbon component can be increased by adding a fresh light hydrocarbon component.

Comparative Example 2

A H-type ZSM-5 zeolite was synthesized by the method described in Example 1 of the description of Japanese Patent Application Laid-open No. H10-052646. The $SiO_2/Al_2O_3$ molar ratio of the resulting zeolite was 42. A zeolite powder of this zeolite was photographed at 15,000× magnification under a scanning electron microscope, and the primary particle size of the zeolite was measured and found to be 1.54 μm.

A molded catalyst containing zinc carried on zeolite, catalyst B-2, was obtained by the same methods as in Example 1.

A reaction was performed in the same way as the catalytic cyclization reaction of Example 3 except that catalyst B-2 was used. The yield of $C_{6-9}$ aromatic hydrocarbons was 45.1% by mass 4 hours after the start of the reaction and 42.7% by mass after 45 hours.

From comparing Example 3 and Comparative Example 2, it is demonstrated that with the conventional H-type zeolite, hot water stability is much less than with the catalyst of the present invention even if the zeolite used is one having the physical properties stipulated in the invention disclosed in Japanese Patent Application Laid-open No. H10-052646. This is because even if the zeolite has a lower $SiO_2/Al_2O_3$ molar ratio (has more reactivity sites), the yield of aromatic hydrocarbons is low at the start of the reaction with an H-type zeolite. This means that more permanent degradation (regeneration degradation) over time is likely in industrial use. In terms of particle size, moreover, the primary particle size of the zeolite is greater than that of the zeolite used in the zeolite-containing molded catalyst of the present invention, meaning that the speed of deterioration (coking deterioration) due to coke precipitation during the reaction is much greater in comparison with the zeolite-containing molded catalyst of the present invention.

Thus, in comparison with previously proposed H-type zeolite catalysts, the zeolite-containing molded catalyst according to the present invention has much better water heat stability as a fine-particle zeolite. Consequently, it is possible to greatly control the conventional problems of regeneration degradation and coking deterioration, and produce aromatic hydrocarbon compounds stably and with high yield over a long period of time.

TABLE 1

[Raw material composition and reaction yields [% by mass] in propylene production step]

| Component | $C_4$ raffinate-2 | Example 1 (yield) | Example 2 (yield) | Example 3 (yield) |
|---|---|---|---|---|
| Hydrogen | 0.00 | 0.04 | 0.05 | 0.04 |
| Methane | 0.00 | 0.18 | 0.26 | 0.22 |
| Ethylene | 0.00 | 6.41 | 9.08 | 7.72 |
| Ethane | 0.00 | 0.15 | 0.21 | 0.18 |
| $C_3H_4$ | 0.10 | 0.00 | 0.00 | 0.00 |
| Propylene | 0.06 | 26.86 | 38.05 | 32.36 |
| Propane | 0.18 | 1.02 | 1.38 | 1.20 |
| Butadiene | 0.91 | 0.03 | 0.02 | 0.03 |
| Butene | 78.95 | 28.91 | 18.31 | 23.90 |
| Butane | 18.48 | 20.57 | 21.45 | 21.00 |
| Pentene | 0.81 | 9.80 | 6.15 | 7.87 |
| Pentane | 0.35 | 0.38 | 0.40 | 0.39 |
| Benzene | 0.00 | 0.13 | 0.19 | 0.16 |
| $C_5$ non-aromatic hydrocarbons | 0.00 | 2.43 | 1.52 | 1.95 |
| Toluene | 0.00 | 0.44 | 0.63 | 0.53 |
| $C_7$ non-aromatic hydrocarbons | 0.00 | 1.35 | 0.85 | 1.08 |
| $C_8$ aromatic hydrocarbons | 0.00 | 0.45 | 0.64 | 0.54 |
| $C_8$ non-aromatic hydrocarbons | 0.16 | 0.47 | 0.29 | 0.38 |
| $C_{9+}$ hydrocarbons | 0.00 | 0.37 | 0.52 | 0.45 |
| Total | 100.00 | 100.00 | 100.00 | 100.00 |
| Diolefin compounds | 1.01 | 0.03 | 0.02 | 0.03 |

TABLE 2

[$C_4$ raffinate-2 and $C_4$+ fraction compositions (% by mass)]

| Component | $C_4$ raffinate-2 | $C_4$+ fraction |
|---|---|---|
| Methylacetylene | 0.07 | 0.00 |
| Propadiene | 0.22 | 0.00 |
| Propylene | 0.18 | 0.01 |
| Propane | 0.04 | 0.00 |
| Butadiene | 1.69 | 0.02 |
| Butene | 78.73 | 7.89 |
| Butane | 17.94 | 4.06 |
| Pentene | 0.30 | 20.47 |
| Pentane | 0.53 | 2.17 |
| Benzene | 0.00 | 2.54 |
| $C_6$ non-aromatic hydrocarbons | 0.00 | 16.15 |
| Toluene | 0.00 | 6.29 |
| $C_7$ non-aromatic hydrocarbons | 0.00 | 16.37 |
| $C_8$ aromatic hydrocarbons | 0.00 | 9.52 |
| $C_8$ non-aromatic hydrocarbons | 0.30 | 7.39 |
| $C_{9+}$ hydrocarbons | 0.00 | 7.12 |
| Total | 100.00 | 100.00 |
| Diolefin compounds | 1.98 | 0.02 |

TABLE 3

[$C_4$ raffinate-2 and $C_5$ fraction compositions (% by mass)]

| Component | $C_4$ raffinate-2 | $C_5$ fraction |
|---|---|---|
| Methylacetylene | 0.02 | 0.00 |
| Propadiene | 0.12 | 0.00 |
| Propylene | 0.06 | 0.00 |
| Propane | 0.05 | 0.00 |
| Butadiene | 2.12 | 0.00 |
| Butene | 76.46 | 0.67 |
| Butane | 20.57 | 0.04 |
| Pentene | 0.22 | 22.55 |
| Pentane | 0.20 | 76.74 |
| Benzene | 0.00 | 0.00 |
| $C_6$ non-aromatic hydrocarbons | 0.01 | 0.00 |
| Toluene | 0.02 | 0.00 |
| $C_7$ non-aromatic hydrocarbons | 0.15 | 0.00 |
| $C_8$ aromatic hydrocarbons | 0.00 | 0.00 |
| $C_8$ non-aromatic hydrocarbons | 0.01 | 0.00 |
| $C_{9+}$ hydrocarbons | 0.01 | 0.00 |
| Total | 100.00 | 100.00 |
| Diolefin compounds | 2.25 | — |

INDUSTRIAL APPLICABILITY

The producing process according to the present invention is applicable in the field of process for producing propylene and aromatic hydrocarbons because it has the effects of allowing propylene and aromatic hydrocarbons to be efficiently and stably produced and also allowing changes in the yield structure by easy methods in the process for producing propylene and aromatic hydrocarbons from a hydrocarbon feedstock containing olefins

Figure 1:
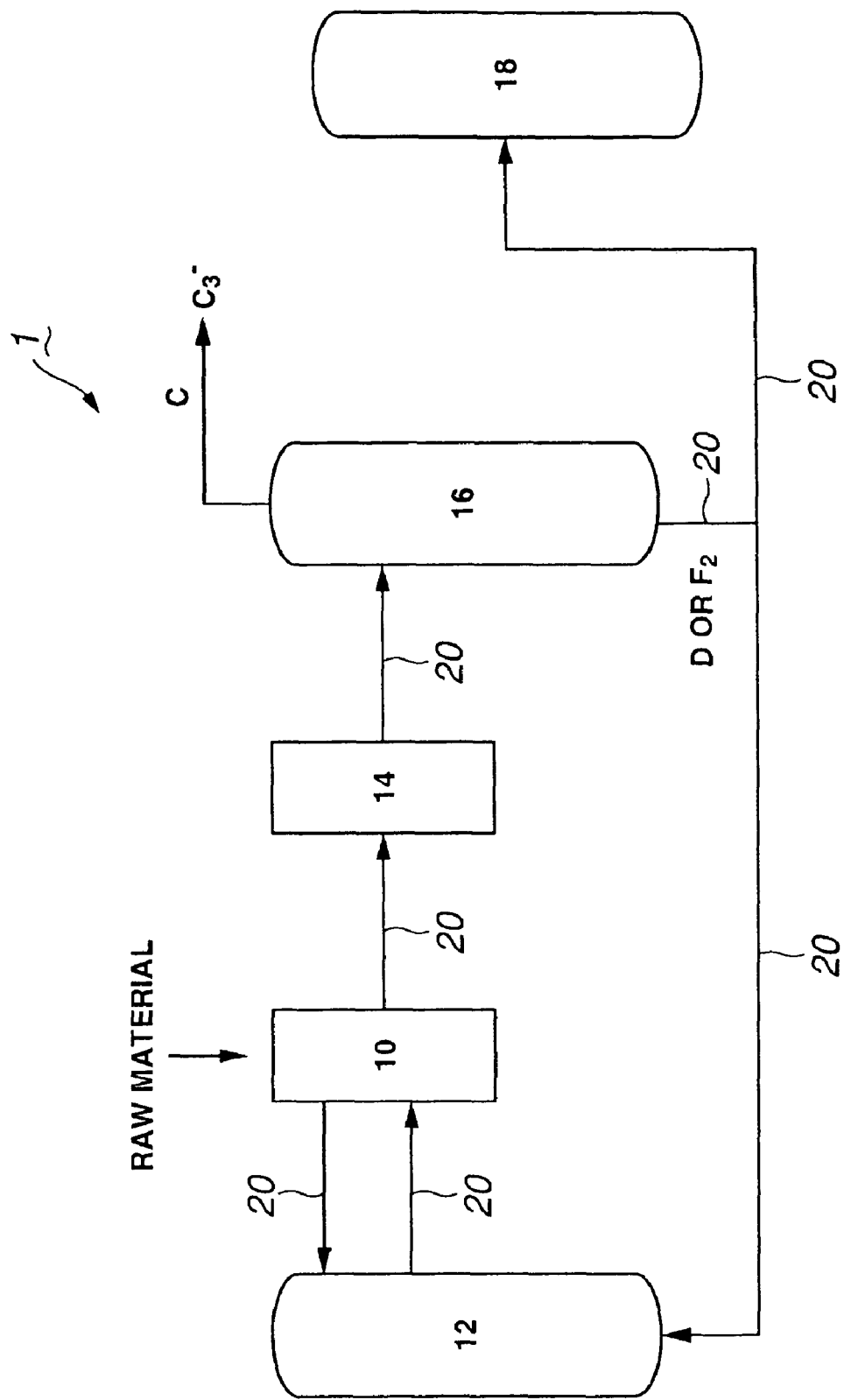
FIG. 1 shows a schematic view of a producing apparatus according to one embodiment for implementing the producing process according to the present invention.
Figure 2:
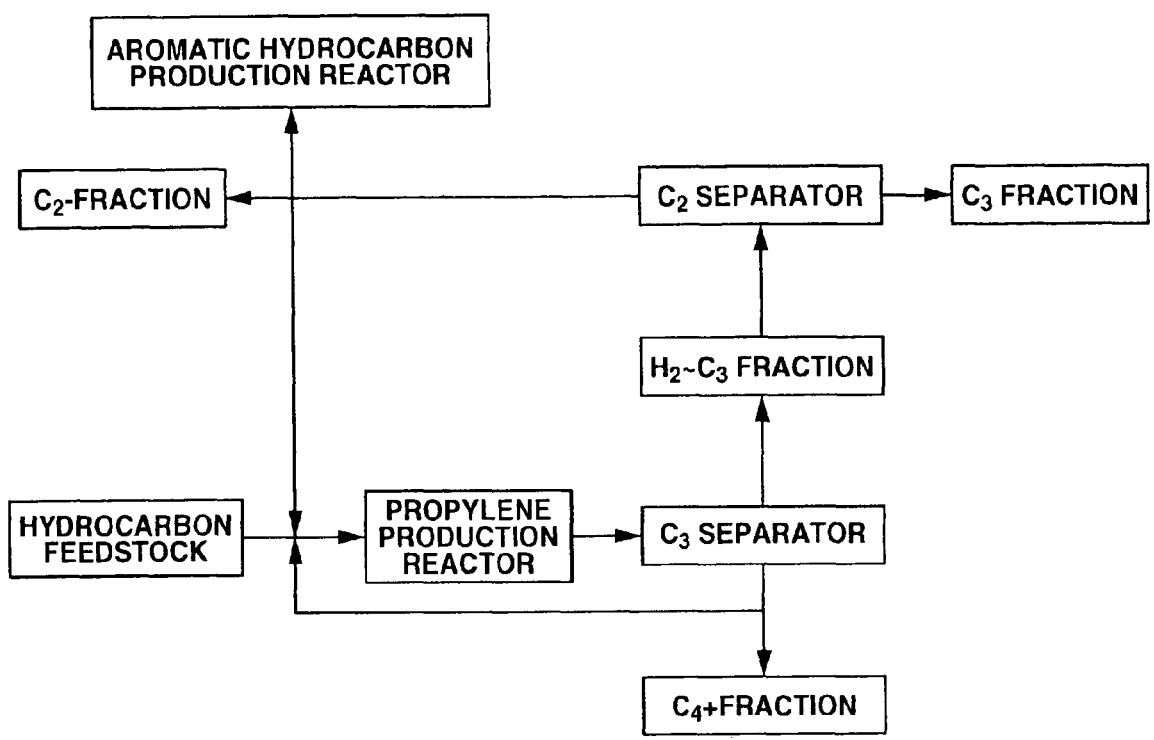
FIG. 2 shows a flow sheet illustrating one embodiment of a system used in the propylene production step of the producing process according to the present invention.
Figure 3:
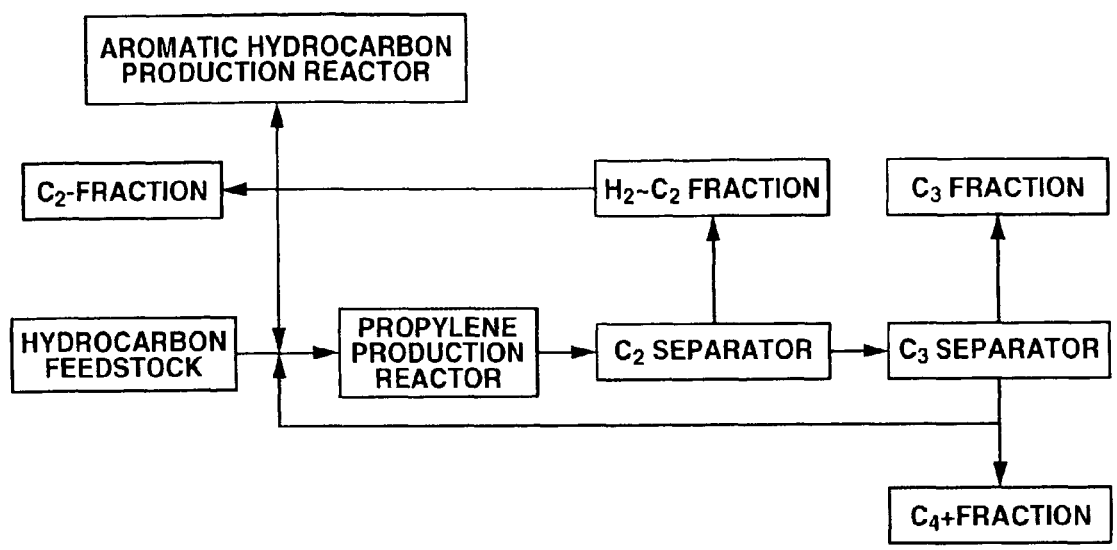
FIG. 3 shows a flow sheet illustrating another embodiment of a system used in the propylene production step of the producing process according to the present invention.

The symbols used in FIG. 1 are defined as follows.
1 . . . Producing apparatus according to the present invention,
10 . . . Heat exchanger,
12 . . . Propylene production reactor,
14 . . . Compressor,
16 . . . Separator,
18 . . . aromatic hydrocarbon production reactor,
20 . . . Conduit

We claim:

1. A process for producing propylene and aromatic hydrocarbons, comprising:
(1) a propylene production step wherein a hydrocarbon feedstock containing 50% by mass or more of at least one of $C_{4-12}$ olefin is brought into contact in a propylene production reactor with a molded catalyst A containing a first zeolite fulfilling conditions (i) through (iv) below to thereby perform a catalytic conversion reaction on the at least one of $C_{4-12}$ olefin, resulting in a reaction mixture containing propylene, the reaction mixture is separated into fraction C containing mainly hydrogen and $C_{1-3}$ hydrocarbons and fraction D containing mainly at least one of $C_{4+}$ hydrocarbon, and propylene is isolated from the fraction C:
(i) having a medium pore diameter zeolite with a pore diameter of from 5 to 6.5 Å;
(ii) containing substantially no protons;
(iii) containing at least one metal selected from the group consisting of metals in Group IB of the periodic table; and
(iv) having an $SiO_2/Al_2O_3$ molar ratio of at least 800 but no more than 2,000; and
(2) an aromatic hydrocarbon production step wherein a raw material containing entirely or partly all or a part of the fraction D is brought into contact in an aromatic hydrocarbon production reactor with a molded catalyst B containing a second zeolite fulfilling conditions (v) through (vii) below in a gaseous phase at 650° C. or less:
(v) having a medium pore diameter zeolite with a pore diameter of from 5 to 6.5 Å;
(vi) with a primary particle diameter in a range of from 0.02 to 0.25 μm; and
(vii) containing at least one metal element selected from the group consisting of metal elements in group IB of the periodic table.

2. The process according to claim 1, wherein the hydrocarbon feedstock containing 50% by mass or more of at least one of $C_{4-12}$ olefin which is used in the propylene production step contains 2.5% by mass or less of at least one of $C_{3-12}$ diolefin compound.

3. The process according to claim 1, wherein the first zeolite contains silver.

4. The process according to claim 1, wherein the first zeolite is an MFI zeolite.

5. The process according to claim 1, wherein a value obtained by dividing an amount of component [% by mass] of the $C_{6-8}$ aromatic hydrocarbons produced in the propylene production reactor by a hydrocarbon partial pressure [MPa] is 13 or less.

6. The process according to claim 1, wherein, in the propylene production step, 10% by mass to 95% by mass of the fraction D is recycled back to the propylene production reactor and used as part of the hydrocarbon feedstock.

7. The process according to claim 1, wherein the fraction C is separated into fraction $C_1$ containing mainly hydrogen and hydrocarbons of 1-2 carbon atoms and fraction $C_2$ containing mainly hydrocarbons of 3 carbon atoms, and at least part of the fraction $C_1$ is recycled back to the propylene production reactor and used as part of the hydrocarbon feedstock.

8. The process according to claim 1, wherein the propylene production reactor is an adiabatic fixed-bed reactor.

9. The process according to claim 1, wherein a reaction temperature for the propylene production step is from 500° C. to 580° C., a partial pressure of the hydrocarbon feedstock is from 0.05 to 0.3 MPa, and a weight hourly space velocity of the hydrocarbon feedstock based on a weight of the molded catalyst A is from 2 $hr^{-1}$ to 20 $hr^{-1}$.

10. The process according to claim 1, wherein the molded catalyst B contains at least one selected from the group consisting of the metals belonging to groups IB, IIB, IIIB and VIII in the periodic table and compounds of these.

11. The process according to claim 1, wherein the second zeolite contains silver.

12. The process according to claim 1, wherein the second zeolite is an MFI zeolite.

13. The process according to claim 1, wherein the aromatic hydrocarbon production reactor is an adiabatic fixed-bed reactor.

14. The process according to claim 1, wherein the fraction C is separated into fraction $C_1$ containing mainly hydrogen and hydrocarbons of 1-2 carbon atoms and fraction $C_2$ containing mainly hydrocarbons of 3 carbon atoms, and at least part of the fraction $C_1$ is used as part of the hydrocarbon feedstock in the aromatic hydrocarbon production step.

15. A process for producing propylene and aromatic hydrocarbons, comprising:
(1) a propylene production step wherein a hydrocarbon feedstock containing 50% by mass or more of at least one of $C_{4-12}$ olefin is brought into contact in a propylene production reactor with a molded catalyst A containing a first zeolite fulfilling conditions (i) through (iv) below to thereby perform a catalytic conversion reaction on the at least one of $C_{4-12}$ olefin, resulting in a reaction mixture containing propylene, the reaction mixture is separated into fraction E containing mainly hydrogen and $C_{1-2}$ hydrocarbons and fraction F containing mainly at least one of $C_{3+}$ hydrocarbon, the fraction F is separated into fraction $F_1$ containing mainly $C_3$ hydrocarbons and fraction $F_2$ containing mainly at least one of $C_{4+}$ hydrocarbon, and propylene is isolated from the fraction $F_1$:
(i) having a medium pore diameter zeolite with a pore diameter of from 5 Å to 6.5 Å;
(ii) containing effectively no protons;
(iii) containing at least one metal selected from the group consisting of the metals in Group IB of the periodic table; and
(iv) having an $SiO_2/Al_2O_3$ mole ratio of at least 800 but no more than 2,000; and
(2) an aromatic hydrocarbon production step wherein a raw material containing entirely or partly all or a part of the fraction $F_2$ is brought into contact in an aromatic hydrocarbon production reactor with a molded catalyst B containing a second zeolite fulfilling conditions (v) through (vii) below in a gaseous phase at 650° C. or less:
(v) having a medium pore diameter zeolite with a pore diameter of from 5 Å to 6.5 Å;
(vi) with a primary particle diameter in the range of from 0.02 μm to 0.25 μm; and
(vii) containing at least one metal element selected from the group consisting of metal elements in group IB of the periodic table.

16. The process according to claim 15, wherein the hydrocarbon feedstock containing 50% by mass or more of at least one of $C_{4-12}$ olefin which is used in the propylene production process contains 2.5% by mass or less of at least one of $C_{3-12}$ diolefin compound.

17. The process according to claim 15, wherein the first zeolite contains silver.

18. The process according to claim 15, wherein the first zeolite is an MFI zeolite.

19. The process according to claim 15, wherein a value obtained by dividing an amount of component [% by mass] of the $C_{6-8}$ aromatic hydrocarbons produced in the propylene production reactor by a hydrocarbon partial pressure [MPa] is 13 or less.

20. The process according to claim 15, wherein, in the propylene production process, 10% by mass to 95% by mass of the fraction $F_2$ is recycled back to the propylene production reactor and used as part of the hydrocarbon feedstock.

21. The process according to claim 15, wherein at least part of the fraction E is recycled back into the propylene production reactor and used as part of the hydrocarbon feedstock.

22. The process according to claim 15, wherein the propylene production reactor is an adiabatic fixed-bed reactor.

23. The process according to claim 15, wherein a reaction temperature for the propylene production step is from 500° C. to 580° C., a partial pressure of the hydrocarbon feedstock is from 0.05 MPa to 0.3 MPa, and a weight hourly space velocity of the hydrocarbon feedstock based on a weight of the molded catalyst A is from 2 $hr^{-1}$ to 20 $h^{-1}$.

24. The process according to claim 15, wherein molded the catalyst B contains at least one selected from the group consisting of metals belonging to groups IB, IIB, IIIB and VIII in the periodic table and compounds of these.

25. The process according to claim 15, wherein the second zeolite contains silver.

26. The process according to claim 15, wherein the second zeolite is an MFI zeolite.

27. The process according to claim 15, wherein the aromatic hydrocarbon production reactor is an adiabatic fixed-bed reactor.

28. The process according to claim 15, wherein at least part of the fraction E is used as part of the hydrocarbon feedstock in the aromatic hydrocarbon production step.

* * * * *

UNITED STATES PATENT AND TRADEMARK OFFICE
CERTIFICATE OF CORRECTION

PATENT NO. : 8,034,987 B2
APPLICATION NO. : 12/086308
DATED : October 11, 2011
INVENTOR(S) : Mitsuhiro Sekiguchi et al.

Page 1 of 1

It is certified that error appears in the above-identified patent and that said Letters Patent is hereby corrected as shown below:

In claim 23, column 34, line 39, "20 $h^{-1}$" should read --20 $hr^{-1}$--.

In claim 24, column 34, lines 40-41, "wherein molded the catalyst" should read --wherein the molded catalyst--.

Signed and Sealed this
Twentieth Day of March, 2012

David J. Kappos
*Director of the United States Patent and Trademark Office*